United States Patent [19]

Poiani et al.

[11] Patent Number: 5,720,950

[45] Date of Patent: *Feb. 24, 1998

[54] POLYMERS CONTAINING ANTIFIBROTIC AGENTS, COMPOSITIONS CONTAINING SUCH POLYMERS, AND METHODS OF PREPARATION AND USE

[75] Inventors: George J. Poiani, Jamesburg; David J. Riley, New Brunswick; Wei-Chi Liao, Princeton Junction; Joachim Kahn; Keria Fiorella Gean, both of Highland Park, all of N.J.

[73] Assignee: University of Medicine & Dentistry of New Jersey, Piscataway, N.J.

[*] Notice: The term of this patent shall not extend beyond the expiration date of Pat. No. 5,372,807.

[21] Appl. No.: 260,080

[22] Filed: Jun. 15, 1994

Related U.S. Application Data

[60] Division of Ser. No. 934,818, Aug. 24, 1992, Pat. No. 5,372,807, which is a continuation-in-part of Ser. No. 864,361, Apr. 6, 1997, abandoned, which is a continuation-in-part of Ser. No. 726,301, Jul. 5, 1991, Pat. No. 5,219,564, which is a continuation-in-part of Ser. No. 549,494, Jul. 6, 1990, abandoned, said Ser. No. 864,361, is a continuation of Ser. No. 523,232, May 14, 1990, abandoned.

[51] Int. Cl.$^6$ .................. A61K 31/765; A61K 9/127
[52] U.S. Cl. .................. 424/78.29; 424/78.17; 424/78.3; 424/450; 424/78.08; 514/824; 528/422; 528/425; 528/288; 528/300; 525/418
[58] Field of Search .................. 528/403, 425, 528/422, 300, 288; 424/78.08, 78.37, 78.29, 78.17, 450, 78.3; 525/418

[56] References Cited

U.S. PATENT DOCUMENTS

| | | | |
|---|---|---|---|
| 549,564 | 6/1895 | Zalipsky et al. | 424/78.17 |
| 4,428,939 | 1/1984 | Prockop | 514/21 |
| 4,672,031 | 6/1987 | Prockop | 436/29 |
| 4,906,476 | 3/1990 | Radhakrishnan | 424/450 |
| 5,219,564 | 6/1993 | Zalipsky | 424/78.17 |
| 5,372,807 | 12/1994 | Poiani et al. | 424/78.37 |
| 5,455,027 | 10/1995 | Zalipsky et al. | 424/78.08 |

FOREIGN PATENT DOCUMENTS 0 080 822  11/1982  European Pat. Off. .

OTHER PUBLICATIONS

S. Zalipsky et al (1983) Eur. J. Polym. vol 19 No. 12 pp. 1177–1183.

Abuchowski et al. "Alteration of immunological properties of bovine serum albumin by attachment of polyethylene glycol." *J. Biol. Chem.* 252 (11): 3578–81. (1977).

Ajisaka et al. "Modification of human hemoglobin with polyethylene glycol: a new candidate for blood substitute." *Biochem. Biophys. Res. Commun.* 97 (3):1076–81. (1980).

(List continued on next page.)

*Primary Examiner*—Peter F. Kulkosky

[57] ABSTRACT

The present invention concerns a method for treating fibrotic conditions by administration of an effective amount of an antifibrotic agent. The antifibrotic agent is preferably a proline analog, such as cis-4-hydroxy-L-proline (cHyp). The antifibrotic agent is operatively linked to a monomer or a polymer, with or without a linking compound, e.g., lysine. Intravenous administration is preferred. The present method facilitates the delivery and release of the antifibrotic agent to inhibit collagen accumulation and thereby to treat fibrosis where collagen metabolism is implicated. A reduced quantity of the antifibrotic agent and a corresponding reduction in the potential for toxicity resulting from prolonged administration thereof may be realized.

10 Claims, 12 Drawing Sheets

OTHER PUBLICATIONS

Bowers–Nemia et al. "A short improved synthesis of N–substituted 5–aza–2–oxa–3–oxo–bicyclo[2.2.1]heptanes." *Heterocycles* 20(5): 817–28. (1983).

Chen et al. "Solubilization and functional reconstitution of the proline transport system of *Eschericha coli.*" *J. Biol. Chem.* 262: 2599–604. (1986).

Ertel te al. "Copolymers of amino acids and poly(ethylene glycol): a new family of functionalized drug–carriers." *Polym. Mat. Sci. Eng.* 66: 486–7. *Proc. Am. Chem. Soc.* (1991).

Kohn et al. "Polymerization Reactions involving the side chains of alpha–L–amino acids." *J. Am. Chem. Soc.* 109: 817–20. (1987).

Nathan et al. "Polyethylene glycol — lysine copolymers: new biocompatible polymers for biomedical applications." *J. Polym. Preprints 1990* 31(2): 213–14 (1990).

Ouchi et al. Synthesis of 5–fluorouracil–terminated monomethoxypoly(ethylene glycol)s, their hydrolysis behavior, and their antitumor activities. *J. Macromol. Sci.–Chem.* A24(9): 1011–32. (1987).

Papaioannou et al. "Simple synthesis of cis–4–hydroxy–L–proline and derivatives suitable for use as intermediates in peptide synthesis." *Acta Chem. Scand.* 44: 243–51. (1990).

Poiani et al. "Intermittent intravenous delivery of antifibrotic agent in liposomes reduces the dose required to prevent hypoxic pulmonary hypertension in the rat." *Am. Rev. Resp. Dis.* 141: A186 (1990) (abstract).

Poiani et al. "Local delivery of liposome–encapsulated proline analogue prevents pulmonary hypertension in the rat." in Amino Acids: Chemistry, Biology and Medicine. Lubec, G. and Rosenthal, eds. pp. 634–642. (1990) (same as *Chem. Abstracts* 115(16): 166492e).

Poiani et al. "An antifibrotic agent reduces blood pressure in established pulmonary hypertension in th e rat". *J. Appl. Physiol.* 68: 1542–47. (1990).

Poiani et al. "Liposome–encapsulated antifibrotic agent prevents early hypoxic pulmonary hypertension in the rat." *Am. Rev. Resp. Dis.* 139: A172. (1989) (abstract).

Prockop. "Regulation of the collagen synthesis in animal cell by Proline and Lysine analogs". *Chem. Abstracts* 78(10): 250, 62201k. (1973).

Prockop, "Controlling cellular synthesis of collagen with cis–L–proline and/or L–lysine derivatives". *Chem. Abstracts* 79(14): 326, 83465k. (1973).

Riley et al. "Effect of proline analogs on oxygen toxicity-–induced pulmonary fibrosis in the rat." *Chem. Abstracts* 101: 23, 204139r. (1984).

Zalipsky et al. "Succinimidyl carbonates of polyethylene glycol: useful reactive polymers for poreparation of protein conjugates." in Polymeric Drugs and Drug Delivery Systems. Dunn et al., ed. *Am. Chem. Soc.* 469: 91–100. (1991).

Zalipsky et al. "Attachment of drugs to polyethylene glycols." *Eur. Polym. J.* 19(12): 1177–82. (1983).

POLYMERS CONTAINING ANTIFIBROTIC AGENTS, COMPOSITIONS CONTAINING SUCH POLYMERS, AND METHODS OF PREPARATION AND USE

This application is a division of application Ser. No. 07/934,818, filed Aug. 24, 1992, and now U.S. Pat. No. 5,372,807 which is a continuation-in-part of application Ser. No. 07/864,361, filed Apr. 6, 1992 and now abandoned; which is a continuation-in-part of application Ser. No. 07/726,301, filed Jul. 5, 1991, and now U.S. Pat. No. 5,219,564; which is a continuation-in-part of application Ser. No. 07/549,494, filed Jul. 6, 1090, and now abandoned; said Ser. No. 07/864,361 also being a continuation of application Ser. No. 07/523,232, filed May 14, 1990, and now abandoned.

The present invention relates generally to the treatment of fibrotic conditions, and to the use of antifibrotic agents for the modification of such diseases.

The fibrotic conditions addressed herein include changes in the structure and function of various organs in connection with the metabolism of collagen and other biomolecules. One of the long-term sequelae of hypertension is the deposition of connective tissue in walls of blood vessels. In hypertensive rats, collagen biosynthesis and deposition are increased in the aorta, and these effects are reversed when blood pressure is lowered by antihypertensive drugs. Treatment of animals with experimental hypertension using agents that selectively inhibit collagen formation and reduce vascular collagen content, suggests that increased collagen contributes to the maintenance of hypertension. Although the use of antifibrotic agents has increased the understanding of the role of collagen in hypertension and vascular disease, their application as potential therapeutic agents for chronic conditions has been limited.

Collagen is the most abundant protein in vertebrates. The biosynthesis of collagen involves unique post-translational modification of pro-alpha chains. Hydroxylation of prolyl and lysyl residues, a key part of collagen formation, is vital for normal triple-helix formation and intermolecular cross-linking. When post-translational processing is inhibited, non-helical procollagen forms which is degraded by intracellular proteases and is secreted into the extracellular matrix at a slower rate as a nonfunctional protein. The incorporation of proline analogues, e.g., cis-4-hydroxy-L-proline (cHyp), into nascent pro-alpha chains reduces the extracellular accumulation of collagen.

The agents described herein are believed to act more generally by inhibiting collagen synthesis and thereby averting certain of the pathophysiological sequelae of fibrosis, such as atherosclerosis and hypertension. Without limiting the invention to a particular mechanism of action, through the distortion of bond angles and from steric hinderance among polypeptide chains, cHyp inhibits the folding of pro-alpha chains into a stable triple helix. Other proline analogues such as cis-4-fluoroproline, cis-4-bromoproline, 3,4-dehydroproline and azetidine-2-carboxylic acid have similar effects, and can also inhibit other post-translational steps. The compounds 3,4-dehydroproline and azetidine-2-carboxylic acid are examples of proline analogues having similar effects, which can also inhibit other post-translational steps. 3,4-dehydroproline inhibits prolyl hydroxylase activity. This proline analogue has been administered to humans with pulmonary fibrosis in adult respiratory distress.

The antifibrotic agents described herein are most effective in tissues undergoing rapid rates of collagen synthesis. For example, collagen comprises about one-third of the dry weight of pulmonary arteries in which synthesis increases rapidly following induction of hypertension. Exposure to hypoxia causes constriction of small pulmonary arteries and hypertension develops from sustained vasoconstriction and structural changes in the vascular wall. Proliferation of vascular smooth muscle cells and connective tissue accumulation thicken the vessel walls and narrow the lumen of pulmonary arteries. These structural changes cause or contribute to hypertension.

Collagen metabolism has been implicated as a negative factor in other diseases and conditions as well. For example, scar tissue is comprised largely of collagen. While some scar tissue deposition is expected as a result of the closure and healing of wounds, excess scar tissue and collagen based adhesions are often undesirable and unhealthy. Several proline analogues have been shown to be effective in inhibiting scar formation.

The present invention in particular relates to monomers and polymers which contain the antifibrotic compounds described herein, pharmaceutical compositions containing such compounds and various methods of preparation and use. In these compounds, cis-hydroxyproline (cHYP) or another antifibrotic agent is the pharmacologically active agent, useful in controlling the proliferation of collagen or the other tissue changes described herein in detail. This is particularly important in diseases and conditions where collagen is deposited or synthesized in abnormally high levels, or where collagen is not properly broken down or removed, contributing to the pathology of the particular disease or condition.

Unfortunately, it is recognized that cHYP can be potentially toxic if used improperly, particularly in chronic use. Thus, this drug has had limited clinical utility.

The present invention seeks to overcome these disadvantages. One object of the present invention is to facilitate the use of antifibrotic agents in the treatment of diseases and conditions in which collagen metabolism is to be modified, such as when excess collagen synthesis or deposition occurs.

Another object of the present invention is to combine the antifibrotic agents described herein with other compounds, e.g., polymers, to improve the pharmacokinetic profile of these drugs.

Another object of the present invention is to combine the therapeutic agents with compounds which have little if any toxicity or side effects of their own.

Another object of the present invention is to enhance the delivery of the antifibrotic agents to the site of activity.

Another object of the present invention is to provide antifibrotic agents in a variety of polymeric and monomeric forms which can be used to modify the pharmacokinetic profile or deliver the agent in question.

These and other objects will be apparent to those of ordinary skill in the art from the teachings herein.

RELATED PUBLICATIONS

The following publications may be of interest to those skilled in the art. These publications are hereby incorporated by reference:

Poiani, G., et al. *Amino Acids: Chem. Biol. & Med.* Lubec, G. and Rosenthal, G. A. (eds) 634–642 (1990).

Poiani, G., et al. *J. Appl. Physiol.* 68: 1542-(1990).

Kohn, J., et al. *J. Am. Chem. Soc.* 109: 817-(1987).

Papaioannu, D., et al. *Acta Chem. Scand.* 44: 243-(1990).

Bowers-Nemia, M. M., et al. *Heterocycles* 20(5): 817- (1983).

Abuchowski, A., et al. *J. Biol. Chem.* 252(11): 3578-(1977).

Ajisaka, K., et al. *Biochem. Biophys. Res. Commun.* 97(3): 1076-(1980).
Ouchi, T., et al. *J. Macromol. Sci.—Chem.*A24(9): 1011-(1987).
Zalipsky, S., et al. *Eur. Polym. J.* 19(12): 1177-(1983).
Zalipsky, S., et al. In Polymeric Drugs and Drug Delivery Systems, Dunn, R. L. and Ottenbrite, R. M., eds. *Am. Chem. Soc.* 469:91 (1991).
Nathan, A., et al. *J. Polym. Preprints* 1990 31(2): 213-(1990).
Ertel, S. I., et al. In *Polym. Mat. Sci. Eng.*American Chem. Soc. 66: 486-(1992).
Additionally, each of the priority applications is hereby incorporated by reference.

SUMMARY OF THE INVENTION

In accordance with one aspect of the present invention, a polymeric antifibrotic agent is disclosed which is comprised of a polymeric backbone and an antifibrotic agent, combined such that the antifibrotic agent is attached to, complexed with or incorporated into the polymeric chain. The polymer can thus be comprised of one or more monomers, prepolymers or antifibrotic agents, and optionally an antifibrotic agent-linking compound. The linking compound is typically an amino acid or a short chain peptide which contains more than one reactive group, or a short chain polyfunctional alkyl compound.

Alternatively, the polymer may be synthesized such that the backbone may incorporate the antifibrotic agent, with or without the linking compound. The antifibrotic agent forms a part of the backbone. In this aspect of the invention, the polymer backbone can be formed from the monomers noted below and the antifibrotic agent.

In accordance with another aspect of the invention, the antifibrotic agent can be operatively linked to a monomer, which may optionally include the linking compound, thus forming a monomeric complex which is comprised of the monomer and the antifibrotic agent optionally linked to the monomer through a linking compound. This embodiment would thus have a low molecular weight relative to the embodiments described above.

The polymeric and monomeric compounds noted above can be included in a pharmaceutical composition in combination with a pharmaceutically acceptable carrier.

The pharmaceutically acceptable carrier may be any of those commonly recognized vehicles used in the formulation of pharmaceutical products.

Another aspect of the invention involves a pharmaceutical composition as described above, wherein the polymer or monomeric unit is used in the pharmaceutically acceptable carrier, and thus serves as a carrier molecule for delivery of the active compound, and as a component in the delivery vehicle. A preferred example of this is in the form of a liposome.

The invention also encompasses a method of treatment of diseases or conditions wherein abnormal collagen metabolism is of concern, comprising administering to a mammalian patient in need of such treatment at least one of the antifibrotic agents described herein in polymeric or monomeric form in an amount effective for treating the abnormality in collagen metabolism.

The diseases and conditions in which the antifibrotic agents described herein are particularly useful include pulmonary conditions, such as pulmonary fibrosis, atherosclerotic conditions, such as arteriosclerosis, renal disorders, such as renal hypertension, hepatic disorders, such as cirrhosis, skin conditions, such as scarring and wrinkling and like conditions.

The invention described herein further includes a process for producing the polymeric or monomeric antifibrotic agents described herein comprising reacting the antifibrotic agent or agents of choice with the monomer or polymer backbone, or with an antifibrotic agent-linking compound, under conditions which do not substantially reduce the pharmacological activity of the antifibrotic agent.

Alternatively, the polymer can be formed, with or without the antifibrotic agent-linking compound, and then the antifibrotic agent condensed with the reactive groups present thereon.

BRIEF DESCRIPTION OF THE DRAWINGS

The invention is described in connection with the following drawings, in which.

DETAILED DESCRIPTION OF THE INVENTION

Figure 1A:
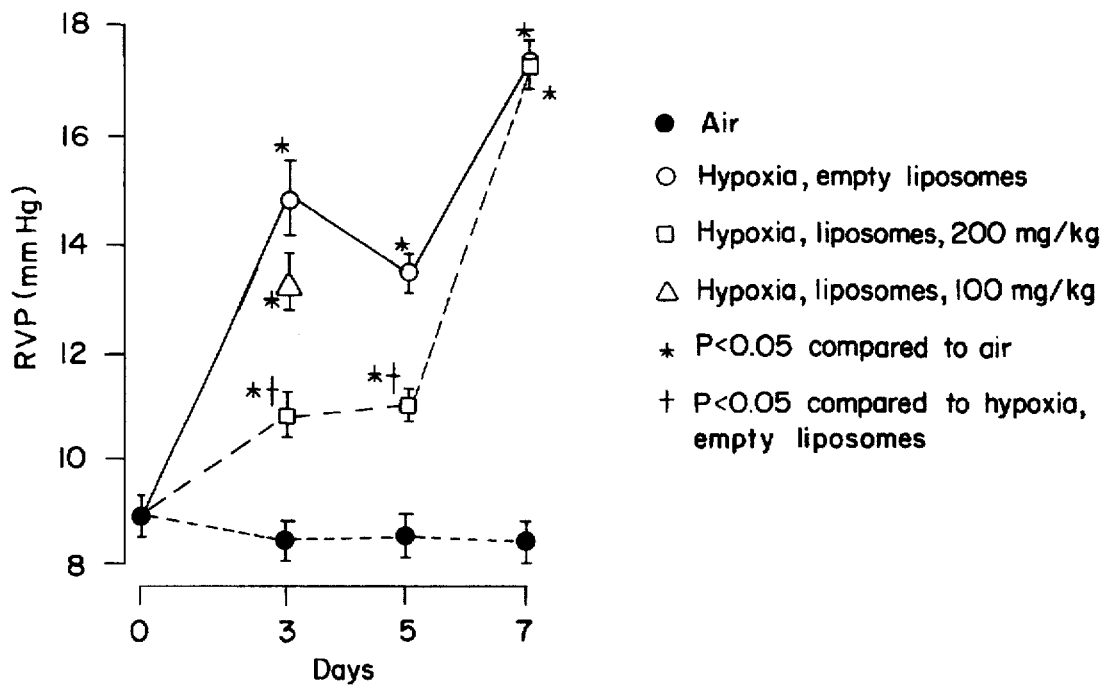
FIGS. 1A–E are graphs depicting the effect of single intravenous injections of cHyp entrapped in liposomes on rats exposed to hypoxia (10% $O_2$) for 7 days. (A) Mean right ventricular pressure. (B) Ratio of ventricular weights. (C) Hematocrit. (D) Hydroxyproline content per vessel. (E) Protein content per vessel. Days indicate days of exposure to air. Data points, mean; bracket, ±SE, n=6–9 for each data point.
Figure 1B:
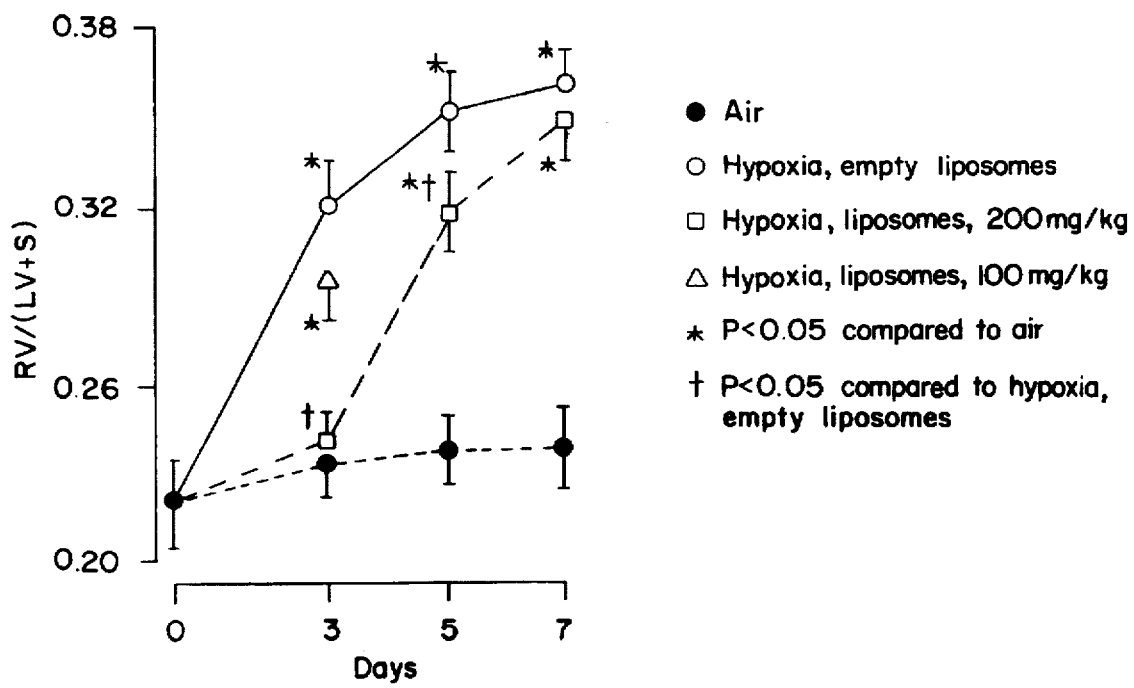
Figure 1C:
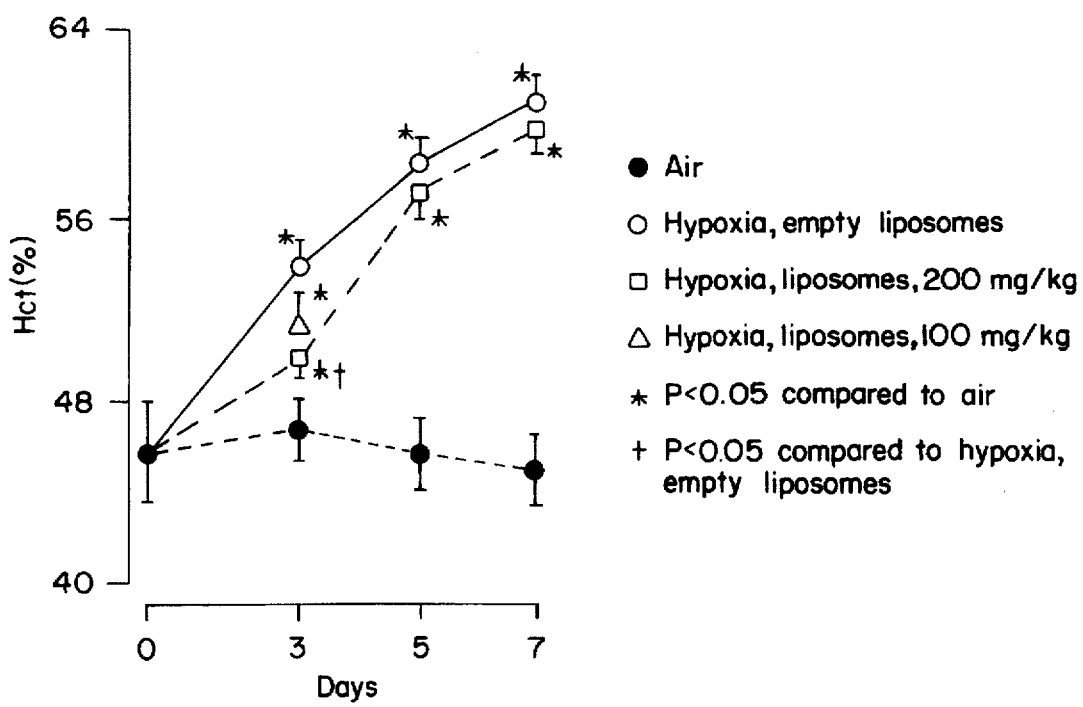
Figure 1D:
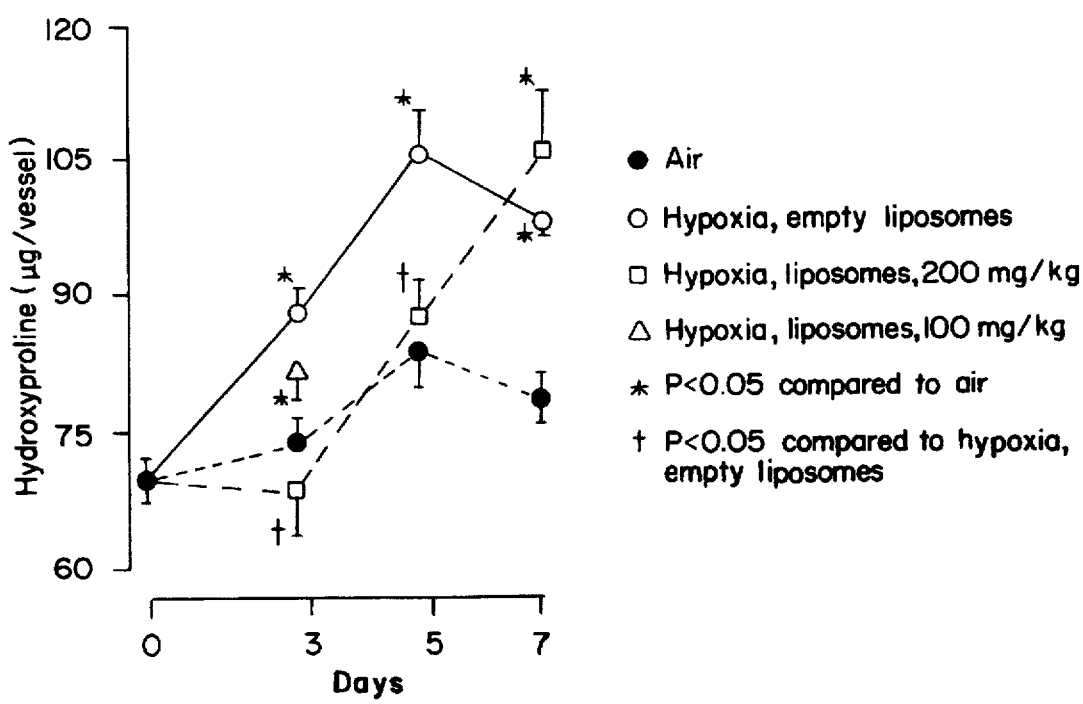
Figure 1E:
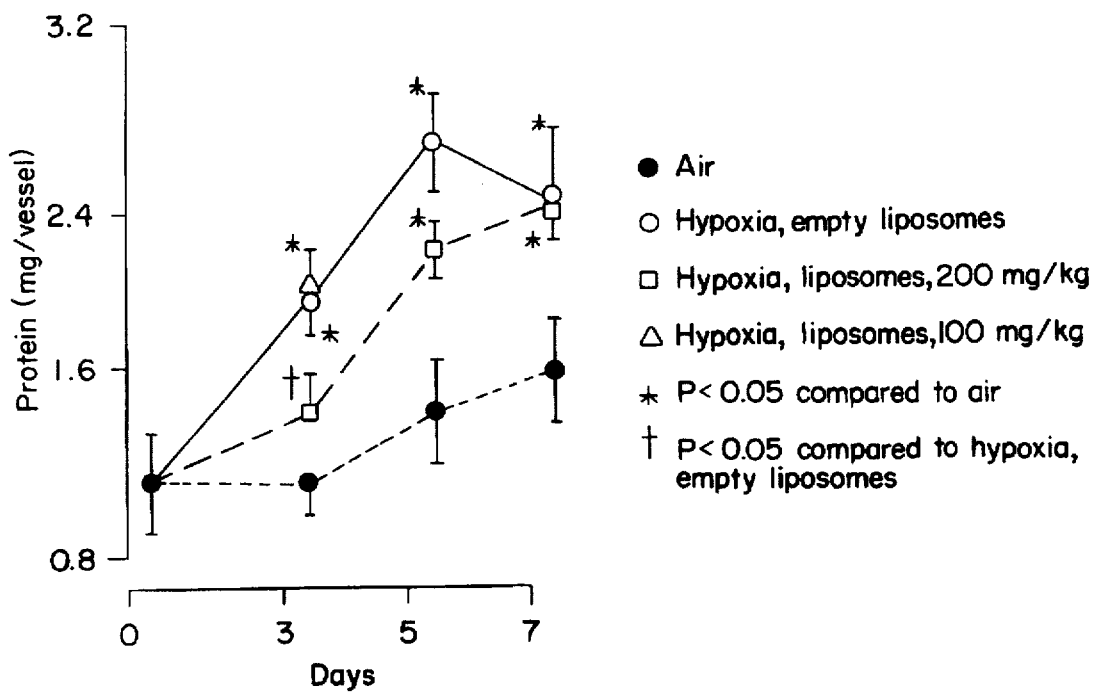
Figure 2A:
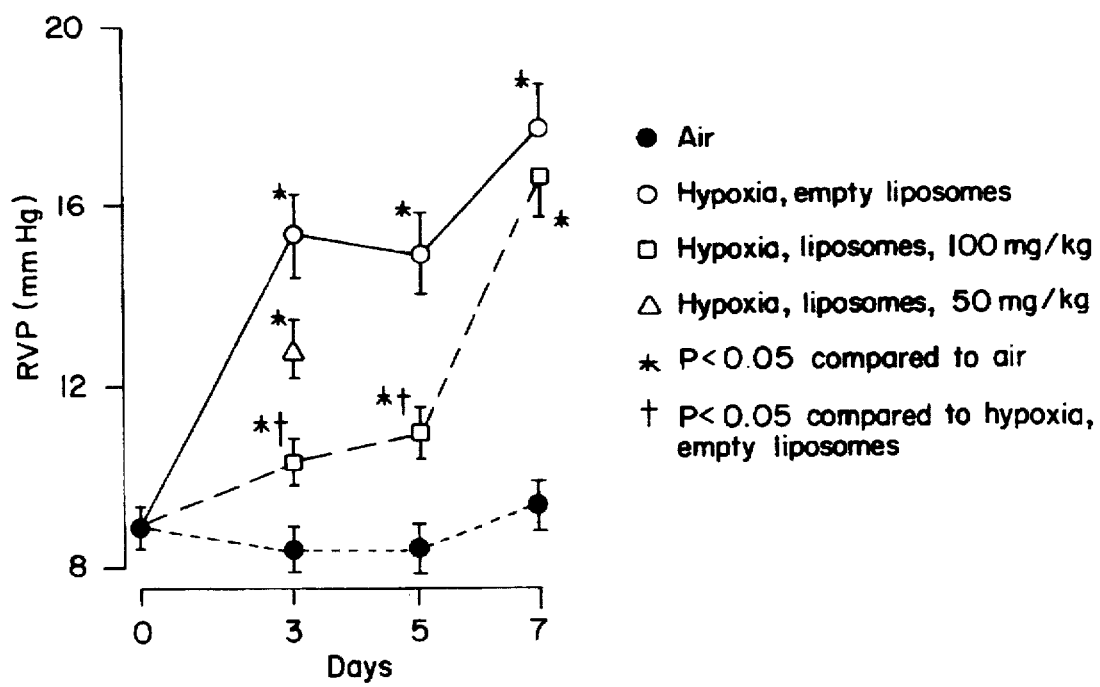
FIGS. 2A–E are graphs depicting the effect of reticuloendothelial blockade with empty liposomes prior to intravenous injection of cHyp entrapped in liposomes on rats exposed to hypoxia (10% $O_2$) for 7 days. Format similar to FIG. 1. n=6–9 for each data point.
Figure 2B:
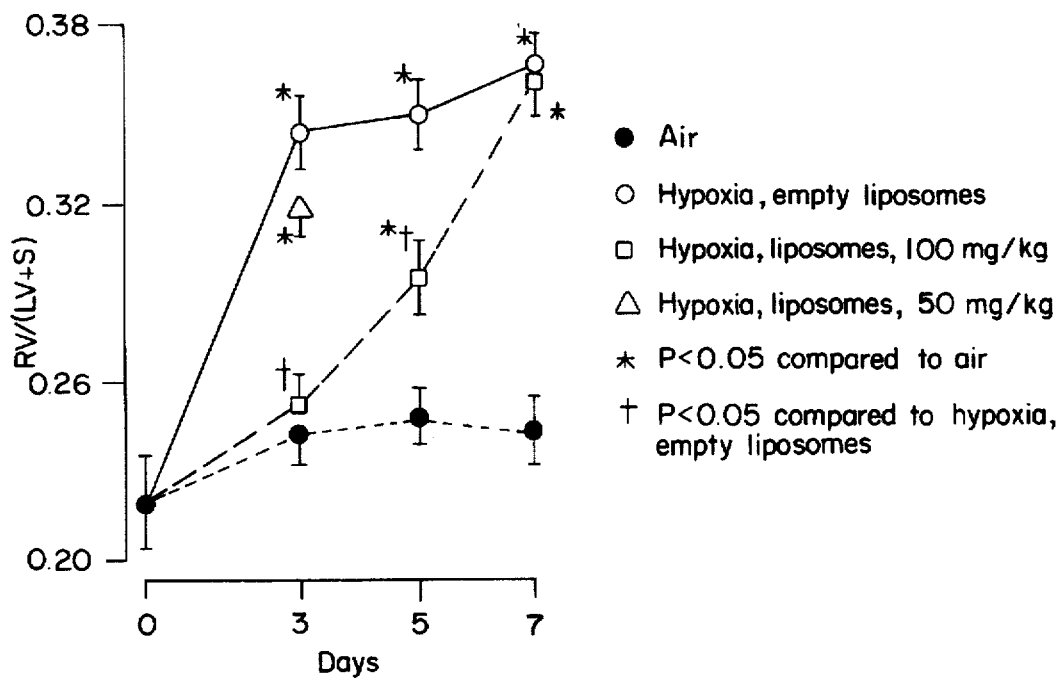
Figure 2C:
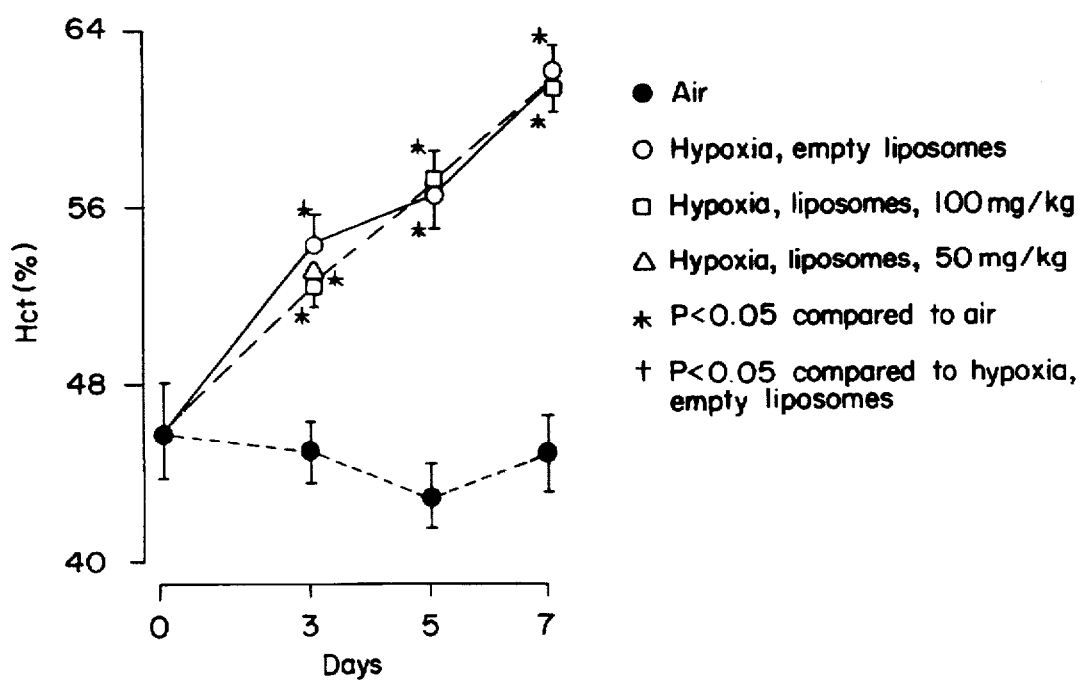
Figure 2D:
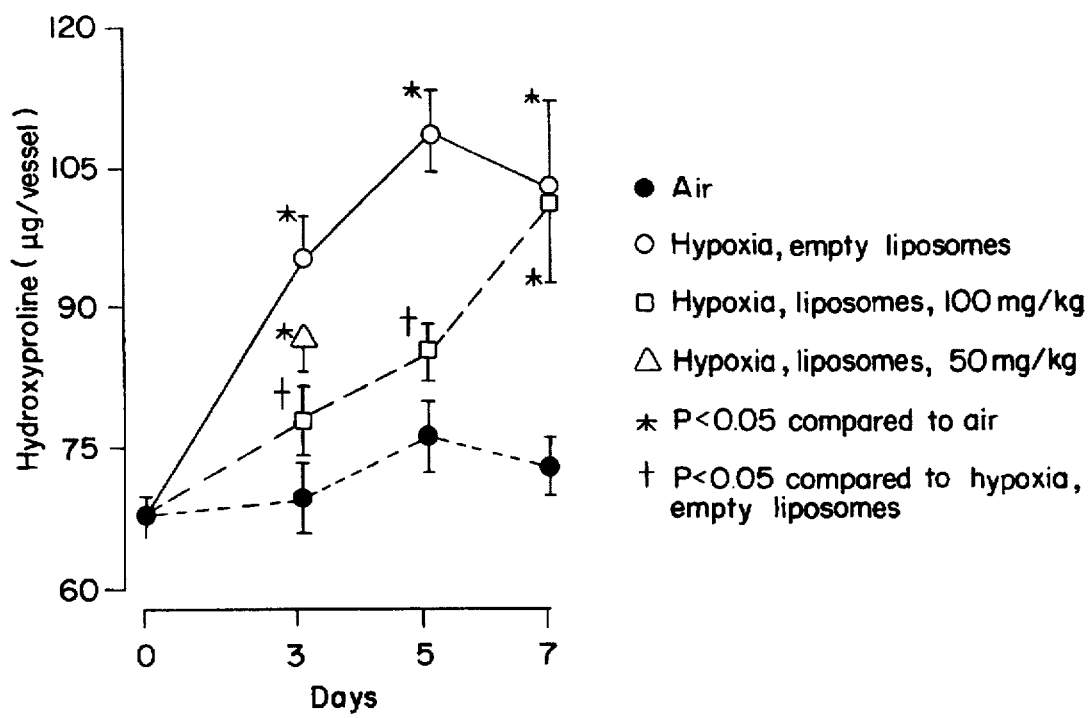
Figure 2E:
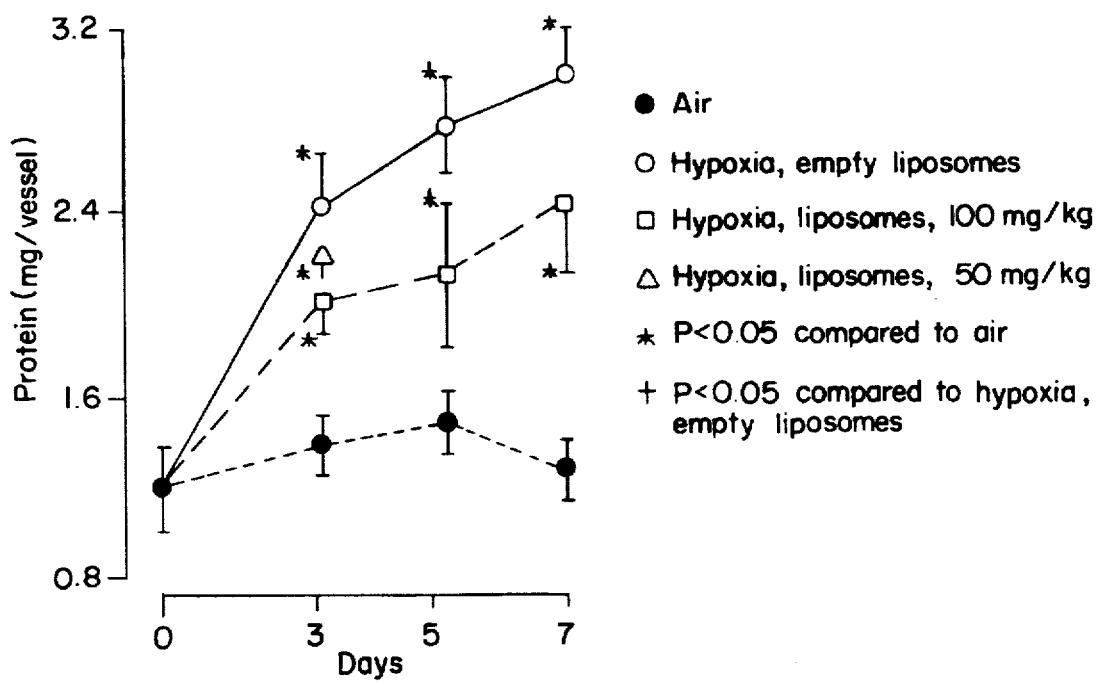

The description contained herein includes numerous terms which are understood by those of ordinary skill, taking into account the following definitions:

The term "antifibrotic agent" refers to chemical compounds which have antifibrotic activity in mammals. This takes into account the abnormal formation of fibrous connective tissue, which is typically comprised of collagen to a greater or lesser degree. These compounds may have different mechanisms of action, some reducing the formation of collagen or another protein, others enhancing the metabolism or removal of collagen in the affected area of the body. All such compounds having activity in the reduction of the presence of fibrotic tissue are included herein, without regard to the particular mechanism of action by which each such drug functions.

It is recognized that certain drugs have been used in the treatment of diseases or conditions which typically accompany fibrotic changes in tissue, such as in the lungs. These overall conditions may be the subject of distinct treatment modalities for sequellae other than the fibrotic changes which are described herein. For example, in the patient with pulmonary fibrosis and pulmonary hypertension, such patients may be treated for the fibrotic changes in the lungs independently from any other treatment which may be rendered for the hypertensive aspects of the overall disease.

The term "backbone" is used to describe the portion of the polymers described herein formed by the polymerization of monomeric units and which typically forms the structural component of the polymer. The backbone may have oneside che side chains attached to it. Both the backbone and the side chains may have functional or reactive groups contained therein or attached thereto. Some polymers described herein include the antifibrotic agent in the backbone, and many of the polymers described herein contain the antifibrotic agent linking compound in the polymer backbone. In certain polymers, particularly branched polymers, there may be little or no difference structurally between the backbone and the side chains, and the distinction between the two may be less significant. In other polymers, there may be a great difference between these portions of the polymer in reactivity, structure and the biological properties attributable thereto.

The term "molecular weight" refers to both number average and weight average molecular weights when used to describe the polymers of the invention. When used to refer to monomers, the antifibrotic agent or the antifibrotic agent-linking compound, the term is used in the conventional sense.

The term "linking compound" is not limited to molecules per se, and refers to compounds, molecules and molecular fragments, e.g., peptides, which can react with the polymer, monomers and antifibrotic agents to attach the antifibrotic agents to the polymer or to incorporate the antifibrotic agents into the polymer. As such, the linking molecule includes compounds and the like with more than one reactive group, preferably two or three reactive groups.

The term "reactive group" refers to chemical moieties which are attached to the polymer or bonds between atoms in the polymer which participate in the chemical reaction between the components involved, e.g., the antifibrotic agent or the linking compound. Examples of reactive groups include without limitation hydroxyl, carboxyl, amine, amide, carbon-carbon double and triple bonds, epoxy groups, halogen or other leaving groups and the like.

The term "pharmaceutically acceptable carrier" refers to those components in the particular dosage form employed which are considered inert and are typically employed in the pharmaceutical arts to formulate a dosage form containing a particular active compound. This may include without limitation solids, liquids and gases, used to formulate the particular pharmaceutical product. Examples of carriers include diluents, flavoring agents, solubilizers, lubricants, suspending agents, binders or tablet disintegrating agents, encapsulating materials, penetration enhancers, solvents, emolients, thickeners, dispersants, sustained release forms, such as matrices, transdermal delivery components, buffers, stabilizers, preservatives and the like. Each of these terms is understood by those of ordinary skill.

When desired, the compounds and compositions of the invention may also utilize liposome technology to facilitate delivery of the medication to the desired site. In this case, the liposome may be viewed as part of the pharmaceutically acceptable carrier. The liposomes may or may not utilize the polymer described herein in the structure thereof. Hence, if the polymer forms part of the liposome, the polymer may also be considered part of the pharmaceutically acceptable carrier itself. If the liposome is comprised of components other than the polymer mentioned above which is linked to or contains the antifibrotic agent, the liposome for purposes of explanation would be considered part of the carrier and the polymer with the antifibrotic agent attached thereto would be treated as the active compound.

Liposomes have been used to deliver drugs locally in concentrated form. For example, liposomes have been used to deliver cHyp intravenously to rats in order to treat experimental pulmonary hypertension and fibrosis. The blood vessels in rats made hypertensive undergo thickening, due in part to the accumulation of collagen in the vessel walls. The thickening and stiffening of these blood vessels contribute to increased resistance to blood flow and ultimately to elevated blood pressure.

The antifibrotic agent may be selected from the group consisting of L-azetidine-2-carboxylic acid; cis-4-hydroxy-L-proline; 3,4-dehydro-L-proline; cis-4-fluoro-L-proline; cis-4-chloro-L-proline; laevo and cis isomers of compounds of the general structural formula:

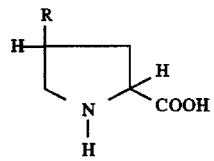

wherein R is OH, Cl, F, NH$_2$, CH$_3$, OC(O)CH$_3$, OC—(O)CH$_2$CH$_3$, SH, SCH$_3$, OCH$_3$, ONO$_2$, OSO$_2$, OSO$_3$H, H$_2$PO$_4$, or COOH; L-pipecolic acid; 1,2,3,6-tetrahydro-L-picolinic acid; 1,2,3,4-tetrahydro-L-picolinic acid; 1,4,5,6-tetrahydro-L-picolinic acid; 1,2,5,6-tetrahydro-L-picolinic acid; 1,2-dihydro-L-picolinic acid; laevo isomers of the compound of the general structural formula:

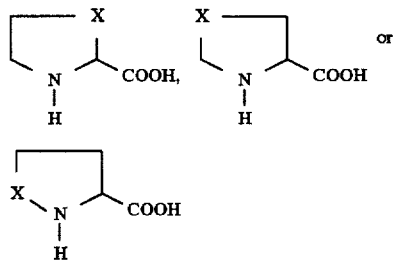

where X is N, S or O; or mixture thereof and a pharmaceutically acceptable carrier therefor.

The preferred antifibrotic compounds include cHYP and its analogs. The most preferred antifibrotic compound is cHYP.

The antifibrotic agents can be operatively linked to the polymer or incorporated into the polymer, to effectuate release thereof over time as the polymer is metabolized.

Operatively linked means joined to the polymer via one or more covalent bonds or combined with the polymer and physically associated therewith without the formation of covalent bonds, such as through ionic attraction or through hydrogen bonding.

The polymers which can be included herein are biocompatible polymers having little or no pharmacologic activity on their own. The polymers, monomers and linking compounds are described in detail in copending application Ser. No. 726,301, now U.S. Pat. No. 5,219,564 which has been incorporated by reference above.

Briefly, the monomers which are useful herein include any functional units which can be covalently bound to the antifibrotic agent, or polymerized to form the backbone of the compounds described herein which can be operatively linked to the antifibrotic agent. For example, preferred monomers include ethylene and ethylene glycol monomers, certain vinylic or polyphenolic type monomers, povidone and povidone derivatives, monosaccharides, and other monomers which have low levels of toxicity and little or no pharmacological activity in and of themselves. The preferred monomers include ethylene glycol, povidone and certain monosaccharides, since these can be reacted with the antifibrotic agent with or without the linking molecule and have desirable solubility characteristics.

Suitable polymers which can be included herein are polymers, comprised in whole or in part of the monomers referred to above. These are referred to in great detail in the copending application. As such, these may poly (oxyalkylene) polyacids, block copolymers of such polyacids with poly(amino acids), polyesters and other types of polymers.

The preferred polymers for use herein are polyalkylene oxides, and in particular, polyethylene and polypropylene glycols which are copolymerized with amino acids or peptide sequences, which can provide pendant functional groups, at regular intervals, for antifibrotic agent attachment or crosslinking.

The preferred poly(alkylene oxides) suitable for use herein include the polymers of polyethylene glycol (PEG), polypropylene glycol, poly(isopropylene glycol), polybutylene glycol, poly(isobutylene) glycol and copolymers thereof. Hence, the backbone of the polymer typically contains straight or branched chain alkyl groups of up to four carbon atoms, with up to about 100 repeating units, with the preferred polymer containing about 10 to 100 repeating units.

The molecular weight of the polymer is not critical, and would depend mainly upon the end use contemplated. In general, the useful number average molecular weight is between about 1,000 and 200,000 daltons, and preferably about 2000 to about 50,000 daltons. Preferably the polymers used herein are hydrolytically stable; in this case, lower molecular weight polymers can be used.

The most preferred polymers and copolymers included herein are the PEGs and PEGs copolymerized with amino acids or peptides having multiple functional groups.

The preferred linking compounds used herein are amino acids and peptides which typically contain saturated or unsaturated straight or branched alkyl groups of up to about six carbon atoms, or alkylphenyl groups, the alkyl portion of which may be covalently bonded to an amine or other functional moiety. The amino acids and peptides containing a low number of amino acids contained therein, e.g., up to about five, preferably are alpha amino acids, which are naturally occurring. The most preferred amino acids are those containing multiple functional groups. The most preferred amino acids are lysine, arginine and cHyp.

Preferred peptides are those which can react with PEG or another polymer and bond via amide, ester or urethane linkages.

To conduct the polymerization reactions referred to above, one can employ various aspects of polymer chemistry to obtain polymers with little variation in the structure or physical parameters. One example of a polymerization technique which can be used to synthesize the polymers noted above is an interfacial polymerization between a water-immiscible organic solution containing one or more activated poly(alkylene) oxides, and a water miscible phase containing one or more amino acids or peptides, having the appropriately protected C-terminals. The aqueous solution is buffered as appropriate, e.g., to a-pH of about 8.0, and the organic phase is added. After reaction, the mixture can be acidified and separated, with the organic phase containing the polymer.

It is also possible to form copolymers noted above using numerous alternative methods and reagents which are well understood.

By selecting the appropriate starting materials, one can form a polymer having free hydroxyl, carboxyl or amino groups which are reactive with the reactive groups present in the antifibrotic agents or with the reactive groups of the linking compounds. For example, when the polymer has pendant carboxyl groups, the antifibrotic agent may be directly conjugated with the carboxyl group via a hydroxyl or amino group. A protection/deprotection reaction scheme can be utilized to block the desired antifibrotic agent reactive groups when multiple functional reactive groups are present may react with the same reagent, and allow the formation of more stable bonds; deprotection can then be undertaken. Likewise, one or more functional groups present on the polymer can be protected.

Using the teachings above, the antifibrotic compounds other than cHyp can be conjugated with the monomers or incorporated into the polymers of the invention in a similar manner.

When the polymer selected does not contain the linking molecule in the backbone, and it contains pendant reactive groups, e.g., carboxyl groups, or if it is otherwise desired, the polymer can be reacted with the linking compound prior to reaction with the antifibrotic agent. For example, pendant carboxyl groups can be reacted with the linking compound, e.g., an alkanolamine, under conditions which favor the formation of either ester or amide bonds between these two compounds, after which the antifibrotic agent is added. The reaction between the polymer carboxyl groups and the linking compound can be conducted in the appropriate solvent and at the appropriate pH to favor the desired functional group formation. After this reaction, if not already in an organic solvent, the components can be transferred to an organic medium and a coupling reagent can be added, e.g., dicyclohexylcarbodiimide (DCC) with any appropriate acylating catalyst to conjugate the antifibrotic agent and the polymer.

The above order of reaction can also be reversed; the drug and the linking molecule are reacted, and then this reaction product is combined with the polymer under appropriate reaction conditions.

Another process for conjugating the polymer and the antifibrotic agent involves the reaction of pendant reactive groups with a compound having aldehyde, ketone or carboxyl groups. The polymer can be combined with a compound which forms acyl hydrazino groups, e.g, hydrazine, and the resulting acyl hydrazino moiety can be linked to the aldehyde, ketone or carboxyl groups, thus forming a hydrazone or diacyl hydrazide linkage between the copolymer and the active compound. Hydrazones can be formed with aldehyde or ketone containing drugs, or by oxidation of carbohydrate residues of glycopeptides.

The polymers noted above can optionally be crosslinked to modify the utility thereof, such as to render the compounds less water soluble. Numerous crosslinking agents can be mentioned as useful herein, including diols and higher polyols, polyamines, polycarboxylic acids, polyisocyanates and the like.

If the polymer is crosslinked, it may be desirable to complex the antifibrotic agent with the polymer rather than covalently bond the active compound to the polymer, either directly or via the linking compound, if adequate delivery of the antifibrotic compound can be realized at the site of activity. Thus, non-covalently bound forms are within the scope of the invention, since the antifibrotic agent is operatively linked to the polymer.

It is also desirable to include the monomers described above reacted with the antifibrotic agent, with or without one or more of the linking molecules included. In this aspect of the invention, the antifibrotic agent can be reacted directly with the monomer via any of the processes detailed above. The monomer is substituted for the polymer and reacted with antifibrotic agent and/or the linking compound. The monomer conjugated with the drug can then be used in the methods of treatment described below.

The method aspects of the invention involve the administration of a polymer or a monomer as noted above to a patient in need of such treatment, in an amount effective to modulate the metabolism of collagen, and thus reduce the formation of fibrotic tissue in the effected area. As mentioned previously, this may entail any of numerous mechanisms of action, such as inhibiting the formation of collagen, enhancing the removal of collagen which is deposited in tissue, or inhibiting the-deposition of collagen which would otherwise form fibrotic tissue.

The compounds may be administered in doses ranging from about 0.05 mg/kg/day to as high as about 1–2 g/kg/day, by any appropriate route of administration, depending upon the particular condition under treatment. The exact dosages will be apparent to those skilled in the medical arts taking into account the teachings contained herein and the overall condition of the patient. Preferably once-daily dosage will be effective in treating patients for the disorders described herein, but divided daily dosages are acceptable as well.

One preferred method of treatment involves the administration of one or more of the polymeric or monomeric antifibrotic agents described above to a mammalian patient with a pulmonary disease or disorder, such as pulmonary hypertension or pulmonary fibrosis. Pulmonary hypertension may accompany pulmonary fibrosis in some patients, or may be found independent of other pulmonary disease, such as in congestive heart failure or other hypoxic conditions. In this method of treatment, the antifibrotic agent may be administered in polymeric or monomeric form via any of the preferred routes of administration, e.g., oral, parenteral, aerosol, e.g., IPPB.

Another preferred method of treatment involves the administration of one or more of the antifibrotic agents described above to a mammalian patient with hepatic disease characterized by a defect in collagen metabolism, e.g, cirrhosis. In this method of treatment, the antifibrotic agent is preferably administered in polymeric or monomeric form, via any route of administration, preferably oral or parenteral.

Another preferred method of treatment involves the administration of one or more of the polymeric or monomeric antifibrotic agents described above to a mammalian patient with a skin disorder wherein collagen metabolism, e.g., excessive deposition is implicated. Examples of such skin disorders include the excess or abnormal formation of scar tissue, wrinkling, scleroderma and other conditions involving the skin. In this method of treatment, the antifibrotic agent is most preferably administered orally, parenterally, topically or transdermally.

Another preferred method involves the treatment of nonspecific vascular disease, e.g., atherosclerosis, wherein the polymeric or monomeric antifibrotic agent is administered to a mammalian patient with atherosclerotic disease in an amount effective to treat abnormal collagen deposition or metabolism. Atherosclerotic disease involves the formation of atherosclerotic plaque and other changes in the vascular tissue, such as thickening of the vessel walls, which may involve collagen to a greater or lesser degree. In this method of treatment, the antifibrotic agent is most preferably administered orally, parenterally, topically or transdermally.

The invention described herein also includes various pharmaceutical dosage forms containing the antifibrotic agents in polymeric or monomeric form. The pharmaceutical dosage forms include those recognized conventionally, e.g., tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

Typically the dosage forms comprise from about 5 to about 70 percent active ingredient per dosage unit. These may be packaged in multiple dose containers or unit dose packages.

Suitable solid carriers are known, e.g., magnesium carbonate, magnesium stearate, talc, lactose and the like. These carriers are typically used in oral tablets and capsules.

Oral liquids may also likely comprise about 5 to about 70 percent active ingredient in solution, suspension or emulsion form. Suitable carriers again are known, and include, e.g., water, ethanol, propylene glycol and others.

Aerosol preparations are typically suitable for nasal or oral inhalation, and may be in powder or solution form, in combination with a compressed gas, typically compressed air. Additionally, aerosols may be useful topically.

Topical preparations useful herein include creams, ointments, solutions, suspensions and the like. These may be formulated to enable one to apply the appropriate dosage topically to the affected area once daily, up to 3–4 times daily as appropriate. Topical sprays may be included herein as well.

Depending upon the particular compound selected, transdermal delivery may be an option, providing a relatively steady state delivery of the medication which is preferred in some circumstances. Transdermal delivery typically involves the use of a compound in solution, with an alcoholic vehicle, optionally a penetration enhancer, such as a surfactant and other optional ingredients. Matrix and reservoir type transdermal delivery systems are examples of suitable transdermal systems. Transdermal delivery differs from conventional topical treatment in that the dosage form delivers a systemic dose of medication to the patient.

A delivery system which may have particular utility in the present invention is one which utilizes liposomes to encapsulate or include the antifibrotic agent. In this system, the liposome may be targeted to a particular site for release of the antifibrotic agent or degradation of the polymeric or monomeric structure to release the active compound. This delivery system thus may obviate excessive dosages which are often necessary to provide a therapeutically useful dose of the drug at the site of activity. In selected experiments, and as set forth in the examples, the effective amount of the antifibrotic agent may be reduced by as much as twenty times the normal effective dose, as indicated by experimental protocols wherein the same antifibrotic agents are administered in free form.

Liposomes may be used herein in any of the appropriate routes of administration described above. For example, liposomes may be formulated which can be administered orally, parenterally, transdermally or via inhalation. Drug toxicity could thus be reduced by selective drug delivery to the effected site using liposomes. If, for example the drug is liposome encapsulated, and is injected intravenously, the liposomes used are taken up by vascular cells, and locally high concentrations of the drug could be released over time within the blood vessel wall, resulting in improved drug action.

The use of liposome encapsulated polymeric and monomeric antifibrotic agents finds utility in the treatment of pulmonary hypertension, and its associated events and sequelae, such as, for example, polycythemia. Liposome encapsulation permits greater quantities of the effective agent to be administered without concomitant toxicity and thereby offers a viable therapeutic alternative.

The liposome encapsulated materials are preferably administered parenterally and, particularly may be administered by intravenous injection. A particularly preferred proline analog is cis-4-hydroxy-L-proline. The proline analogs of the present invention are generally disclosed in U.S. Pat. No. 4,428,939, issued Jan. 31, 1984 to Darwin J. Prockop, the disclosure of which is incorporated herein by reference. Such compounds are illustrative of antifibrotic agents useful in accordance with the present invention.

It has been demonstrated that twice daily subcutaneous injections of 200 mg/kg cHyp ameliorates development of chronic hypoxia-induced hypertension in rats. Since prolonged treatment with cHyp causes toxicity in adult rodents, localized delivery of cHyp to hypertensive pulmonary arteries has been achieved by encapsulation in phospholipid based liposomes. Rats with experimentally induced pulmonary hypertension have been successfully treated with liposome-encapsulated cHyp, reducing the effective dose of drug substantially, and causing sustained inhibition of vascular collagen accumulation.

The invention can be further illustrated in connection with the following Examples. For purposes of illustration, when a PEG copolymer is reacted with lysine, the following poly(PEG-Lys) copolymer may be formed:

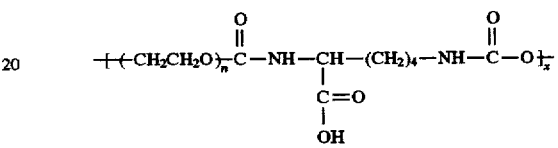

Likewise for purposes of illustration, the following reaction schemes are included within the preferred processes of making the cHyp based polymers of the present invention. Scheme 1 involves the preparation of poly(cis-N-palmitate-Hyp)ester and is the subject of Example 13 below. The trans-N-palmitoyl hydroxyproline is reacted with triphenylphosphine and a dehydrating agent to form a bicyclic compound, which in turn opens and rearranges to the cis form, which can be polymerized. Scheme 2 involves the preparation of monomethoxy-PEG-cHYP conjugates, and is described in detail in Example 14. Scheme 3 illustrates the preparation of poly(PEG-Lys)-cHyp copolymers, and is described in detail in Example 15.

Scheme 1: Preparation of poly(cis-N—Pal—Hyp ester).

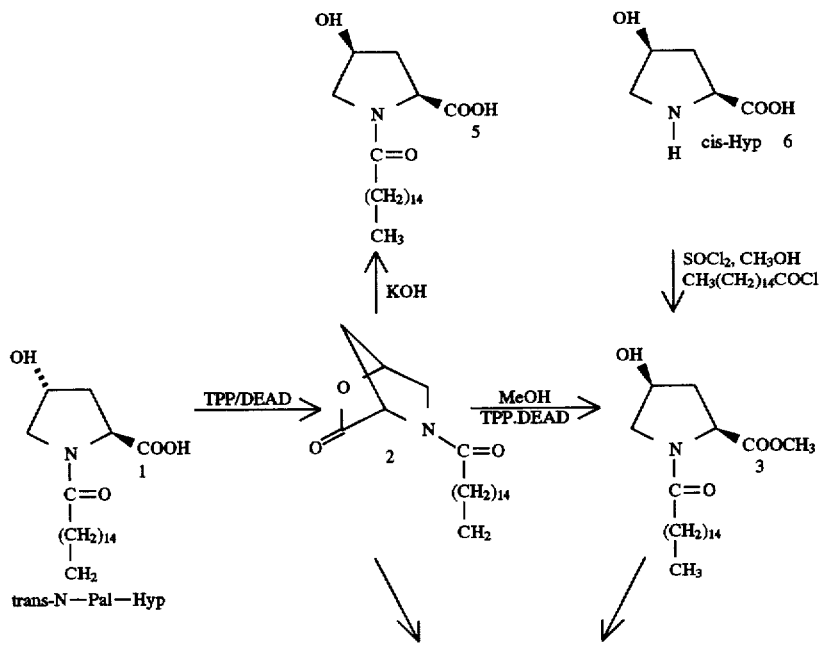

-continued
Scheme 1: Preparation of poly(cis-N—Pal—Hyp ester).

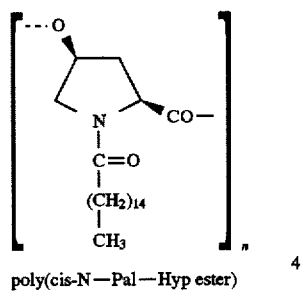

poly(cis-N—Pal—Hyp ester)
15

Scheme 2: Preparation of monomethoxy-PEG-cis-Hyp conjugates.

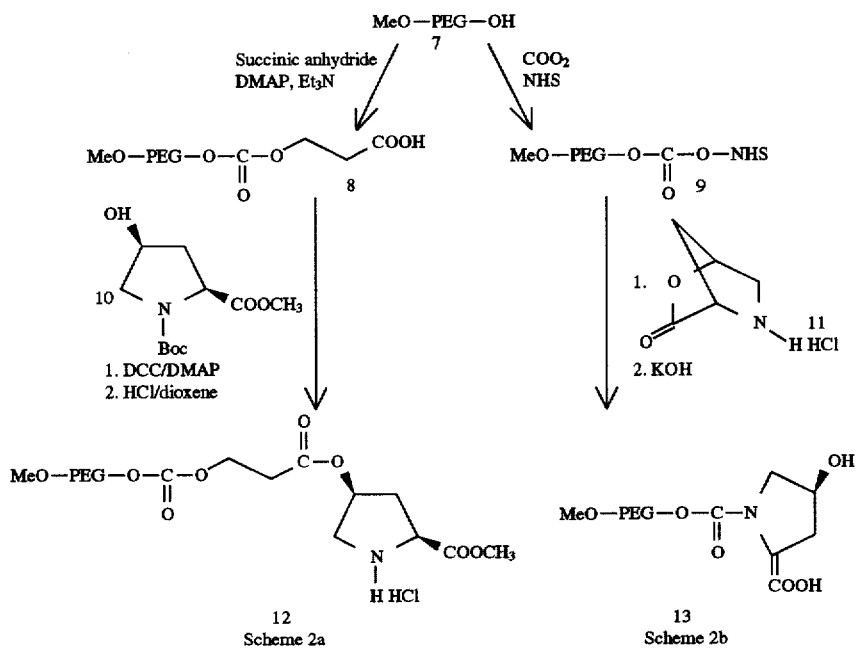

Scheme 3: Preparation of poly(PEG—Lys)cis-Hyp copolymers.

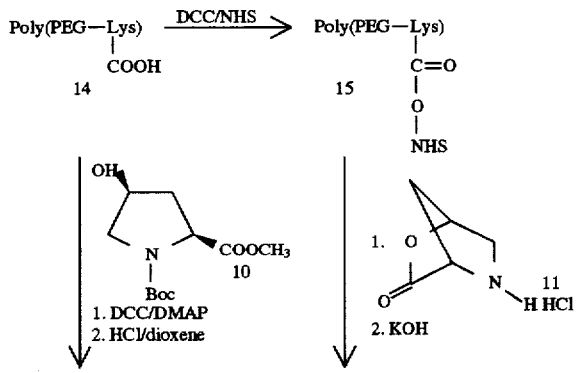

-continued
Scheme 3: Preparation of poly(PEG—Lys)cis-Hyp copolymers.

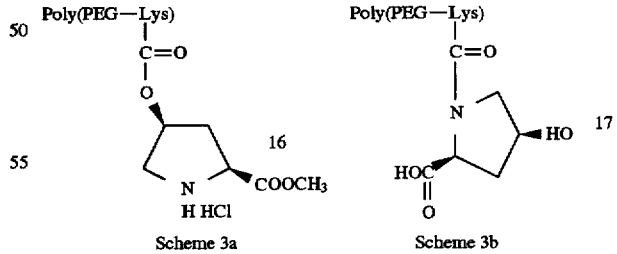

EXAMPLE 1

Preparation of PEG-Bis Succinimidyl Carbonate

The preparation of PEG-bis succinimidyl carbonate is disclosed in U.S. application Ser. No. 340,928. In a 250 mL round bottomed flask, 10 g (10 mmols of hydroxy groups) of PEG 2000 (Fluka) was dissolved in 120 mL of toluene and th polymer solution was azeotropically dried for two hours under reflux, using a Dean-Stark trap. The polymer solution was then cooled to 25 degrees C. and 15 mL (29 mmol) of a 20 percent solution of phosgene in toluene (1.93M) was added. The reaction mixture was stirred at 25° C. overnight and then evaporated to dryness on a rotary evaporator (water bath temperature maintained at 40° C.). Another 100 mL of toluene was added and evaporated to remove all traces of phosgene. To the polymeric chloroformate was added 30 mL of dry toluene, 10 mL of methylene chloride, and 1.7 g (14.8 mmol) of N-hydroxy succinimide, and the mixture was stirred vigorously. The reaction flask was then cooled in an ice water bath and 1.5 g (14.9 mmol) of triethylamine was added gradually. Immediate precipitation of triethylamine hydrochloride was seen. The cooling bath was removed and the stirring continued at 25 degrees C. for five hours. Then 10 mL of toluene was added and the reaction mixture cooled to 4 degrees C. to maximize the triethylamine hydrochloride precipitation.

The precipitate was filtered and the filtrate concentrated to about half of its original-volume. The concentrated solution was then added to 60 mL of ether with stirring to precipitate the polymeric product. After cooling to 40 degrees C., the crude product was recovered by filtration, dried, redissolved in 100 mL of 2-propanol at 45 degrees C. and allowed to recrystallize. The product was recovered by filtration, washed with ether and dried under high vacuum. The recovery of the white crystal and solid was 74 percent.

EXAMPLE 2

Preparation of PEG-Lysine Ethyl Ester Copolymer (Poly(PEG-Lys-OEt)

In a 500 mL three-necked round-bottomed flask fitted with an overhead stirrer was dissolved 1.1 g (4.4 mmol) of lysine ether ester hydrochloride salt (Fluka) and 1.7 g (21 mmol) of sodium bicarbonate in 100 mL of water. The PEG-N-hydroxy succinimide-dicarbonate of Example I (10 g, 4.4 meq) was dissolved in 200 mL of methylene chloride and added to the reaction mixture. The mixture was stirred vigorously (about 1100 rpm) for two hours and then acidified to about pH 2. The two phases were separated and the organic phase was washed twice with NaCl. The organic layer was then dried over anhydrous MgSO4, filtered and concentrated. The polymer was precipitated using cold ether, cooled to 40 degrees C. and filtered to recover 6.7 g (67 percent) of the polymer.

The crude polymer (500 mg) was dissolved in 10 mL of distilled water and dialyzed against distilled water at room temperature for 48 hours using a SPECTRAPOR(tm) membrane with a molecular weight cut-off of 12,000 to 14,000 daltons. The purified polymer was extracted with methylene chloride, washed with saturated NaCl solution, dried and evaporated to obtain 263 mg (53 percent) of pure polymer.

EXAMPLE 3

Preparation of PEG-Lysine Copolymer Poly(PEG-Lys)

The polymer of Example 2 (5 g) was dissolved in 5 mL of $H_2O$. The pH of the polymer solution was about 5 as measured with a pH meter. A 0.01N NaOH solution was prepared, and the base was added dropwise into the polymer solution with stirring. The pH was monitored continuously and kept around 11.5 by the addition of base as needed. The reaction was allowed to go for five hours. The reaction was stopped and the reaction mixture was acidified with 0.1N HCl. The polymer was extracted into methylene chloride and the extract was washed with saturated Nacl, dried over anhydrous MgSO4, filtered and concentrated. The polymer was then precipitated with cold ether. After cooling for several hours, the product was collected in a Buchner funnel, washed with cold ether and dried under vacuum overnight. 3.5 g of polymer (71 percent) was recovered.

EXAMPLE 4

Preparation of Activated Poly(PEG-Lys)

In a 10 mL round-bottomed flask, 1.0 g (0.46 mmol) of the polymer of Example 3 was dissolved in 5 mL of methylene chloride. To this solution, 0.26 g of N-hydroxysuccinimide (Aldrich) (2.3 mnol) was added. The flask was cooled in an ice water bath and 0.10 g (0.50 mmol) of dicyclohexylcarbodiimide (DCC) (Aldrich) was added. The reaction mixture was then stirred at 0 degrees C. for one hour and at room temperature overnight. The reaction mixture was filtered to remove dicyclohexyl urea and the methylene chlorine was evaporated to give a white, waxy material.

Isopropanol (5 mL) was added and the mixture was stirred until a clear solution was obtained. Cooling to −15 deg C. precipitated a white solid which was collected on a Buchner funnel and washed first with isopropanol and then with hexane. The material was further purified by recrystallization from isopropanol. The recovery of the final product was 0.72 g (71 percent).

EXAMPLE 5

Preparation of Poly(PEG-Lys) with Pendant Acyl Hydrazine Functional Groups

In a 50 mL round-bottomed flask, 2.2 g (1.0 mmol) of the polymer of Example 3 was dissolved in 20 mL of methylene chloride. The flask was then cooled in an ice water bath. To the flask were added 410 mg (2.0 mmol) of DCC and 260 mg (2.0 mmol) of tert-butyl carbazate (Aldrich). The contents of the flask were stirred at ice water bath temperature for 1 hour and then stirred at room temperature for 24 hours. The reaction mixture was filtered to remove the dicyclohexyl urea, followed by evaporation of the filtrate to dryness, which gave 1.5 g of light solid that was purified by recrystallization from 2-propanol. The $^1H$ proton NMR spectrum of the white, waxy solid showed tert-butyl peaks, the area of which corresponded to greater than 90 percent conversion. When redissolved in methanol and reprecipitated with ether, the relative intensity of this peak did not decrease.

An approximate 4M solution of HCl in dioxane was prepared by bubbling HCl gas through dioxane in an Erlenmeyer flask (a 4.0M solution is also available commercially from (Pierce). In a 250 mL round-bottomed flask was placed 75 mL of the 4.0M HCl/dioxane solution, and to this was added with stirring 5.0 g of the polymer-carbazate reaction product in the form of small pieces. Stirring was continued for two hours at room temperature. The polymer settled at the bottom of the flask as an oil. The dioxane/HCl layer was decanted out and the polymer layer was added to 100 mL of the ether with stirring. The polymer precipitated and was isolated, washed twice with 50 mL of ether and dried under vacuum. It was further precipitated by recrystallization from isopropanol.

The $^1H$ NMR spectrum of the product showed the complete absence of tert-butyl groups. Non-aqueous titration against sodium methoxide with methyl red as the indicator showed about 100 percent of the expected hydrochloride.

EXAMPLE 6

Preparation of Poly(PEG-Lys) Having Ethanol Amide Pendant Functional Groups

In a 50 mL round-bottomed flask, 0.400 g (0.1819 mmol) of the poly(PEG-Lys) of Example 3 was dissolved in 40 mL of water. To this solution was added 0.1 mL (1.656 mmol) of ethanol amine (Aldrich). The pH was adjusted to 4.75 by the addition of 0.1N HCl. Then 0.348 g (1.82 mmol) of solid 1-(3-dimethylaminopropyl-3-ethylcarbodiimide) (Sigma) was added. The pH had a tendency to increase, but was maintained around 4.75 by the addition of 1N HCl. After 30 minutes, no further increase in pH was observed. The reaction mixture was stirred overnight and then acidified and extracted into methylene chloride. The methylene chloride extract was washed with saturated sodium chloride solution, dried with anhydrous magnesium sulfate, filtered, concentrated to a viscous syrup and precipitated with cold ether. About 0.318 g of crude poly(PEG-Lys) with ethanol amide pendant functional groups was recovered. The crude product was purified by reprecipitation from isopropanol, followed by washings with hexane and complete drying in vacuo. Thin layer chromatography (TLC) in a 4:1 ratio solution of ethanol to ammonia showed an absence of free ethanolamine.

EXAMPLE 7

Preparation of Poly(PEG-Lys) Having Ethylamine Pendant Functional Groups

In a 100 mL three-necked flask, 1.21 g (0.55 mmol) of the poly(PEG-Lys) of Example 3 was dissolved in 80 mL of water. To this solution was added 0.37 mL (5.5 mmol) of ethylene diamine (Aldrich). The pH was adjusted to 4.75 by the addition of 1N HCl. Then 1.05 g (5.5 mmol) of solid 1-(3-dimethylaminopropyl-3-ethylcarbodiimide) was added. The pH had a tendency to increase, but was maintained around 4.75 by the addition of 1N HCl. After 30 minutes, no further increase in pH was observed. The reaction mixture was stirred overnight and then made basic and extracted into methylene chloride. The methylene chloride extract was washed with saturated sodium chloride, dried with anhydrous magnesium sulfate, filtered, concentrated to a viscous syrup and precipitated with cold ether. About 0.725 g of crude poly(PEG-Lys) having ethylamine pendant functional groups was recovered, which was purified by reprecipitation with isopropanol. TLC in a 2:1 solution of ethanol to ammonia showed an absence of free diamine.

EXAMPLE 8

Preparation of Poly(PEG-Lys) Having Pendant Hexylamine Functional Groups

The procedure of Example 7 was followed substituting 5.5 mmol of hexamethylene diamine (Aldrich) for the 5.5 mmol of the ethylene diamine. Upon purification of the product, TLC in a 2:1 ratio ethanol to ammonia solution showed an absence of free diamine.

EXAMPLE 9

Preparation of N-Benzylcarbamate Derivative of a Copolymer of PEG and Glutamic Acid 2 g of PEG 2000 was azeotropically dried following the procedure of Example 1 by dissolving the polymer in 30 mL of toluene in a preweighed 50 mL round-bottomed flask provided with a stirrer. The polymer solution was azeotropically dried for two hours under reflux in an oil bath, the temperature of which was maintained at 140 degrees C. All the solvent was distilled off and the product was dried under vacuo. The dried PEG was reweighed, dissolved in 5 mL of methylene chloride and stirred under argon. An equimolar amount of glutamic acid, the N-terminal of which was protected by a benzylcarbamate functional group (Sigma) was added. Four times this amount of diisopropylcarbodiimide (Aldrich) and four times this amount of dimethylaminopyridinium toluene sulfonate (Aldrich) were added. The reaction mixture was heated slightly to dissolve the glutamic acid. The reaction was allowed to run for 24 hours at room temperature with stirring. A urea precipitate formed that was removed by filtration, and the product was precipitated by cold ether, filtered and dried under vacuum. About 1.6 g of polymer was recovered, which was purified by reprecipitation from isopropanol. TLC in a 5:5:1 ratio solution of toluene to acetic acid to water showed the absence of free glutamic acid.

EXAMPLE 10

Preparation of Poly(PEG-Lys) Cross-Linked by Hexamethylene Diisocyanate

A mold was prepared by clamping two square glass plates together, one of which had a 5 cm diameter circular cavity. The contacting surfaces of the glass plates were coated with trimethylchlorosilane (Aldrich) to prevent adhesion. The mold was placed on a level surface inside a glove box and further leveled using a carpenter's level. In a 100 mL beaker, 1.5 g of the poly(PEG-Lys) having pendant acyl hydrazine groups (0.67 mmol of hydrazine groups) of Example 5 was dissolved in 40 mL of methylene chloride. To this solution w&s added 1.5 g of finely powdered sodium bicarbonate. The suspension was stirred for one hour and the supernatant was tested for the presence of chloride ions with silver nitrate. A few drops of the methylene chloride solution were placed into a test tube, the methylene chloride was evaporated, and the residue was reacted with a few drops of silver nitrate solution acetified with nitric acid. The absence of any white turbidity indicated the complete neutralization and removal of hydyochloric acid.

The solution was then filtered and the residue was washed with methylene chloride. To the combined filtrate, 54 microliters of hexamethylene diisocyanate (56 mg., 0.67 meq of isocyanate groups) (Aldrich) was added with stirring. After two to three minutes of stirring, the solution was poured into the circular cavity of the solvent casting mold. The cavity of the mold was covered with filter paper so that the solvent evaporation was slow and uniform. The film was allowed to dry in the glove box for 48 hours and then peeled from the mold. The thickness of the membrane was measured with an electronic vernier caliper inside the glove box and was found to be about 0.1 mm.

The membranes obtained were semi-transparent and were somewhat hygroscopic, curling up when exposed to moisture in ambient air. When placed in water, the size of the films doubled in all dimensions, indicating a very large swelling ratio. The swollen membranes were transparent.

The membrane was assayed with trinitrophenyl sulfonic acid (TNBS) (Fluka) to determine the extent of crosslinking. An excess of TNBS was used, and after reacting with the polymer, the unreacted TNBS was allowed to react with an excess of adipic hydrazide. The IR absorbance obtained at 500 nm was then used to calculate the amount of free hydrazides present on the cross-linked membrane. Using this method, it was found that 80–85 percent of all available hydrazides precipitated in cross-linking, leaving only 15–20 percent of unreacted hydrazides on the cross-linked membrane.

Calorimetry of the cross-linked membrane showed a sharp endothermic transition at 33.4 deg C. This is very similar to the $T_m$ of the corresponding non-cross-linked poly(PEG-Lys) having pendant acyl hydrazine functional groups (34.1 deg C.). When the membrane was heated in an oven above the phase transition temperature, it became very flexible but did not disintegrate. These results indicate that the properties of PEG dominate even after copolymerization with lysine and cross-linking.

Swelling measurements of the membrane were made by two methods. The dimensions of the dry membrane were measured and the membrane was allowed to swell in water. The increase in dimension was taken as a measure of swelling. Alternatively, the membrane was weighed before and after swelling and the increase in weight was taken as a measure of swelling. Both methods indicated that the membrane absorbs about 5 to 8 times its weight of water.

The tensile strength of the membrane was measured using strips of membrane 0.07 mm thick, 5 mm wide and 50 mm long. Measurements were made employing both dry and swollen membranes.

In the swollen state, the membrane behaves like a perfect elastomer. The membrane did not exhibit a yield point and a plot of stress against strain gave a straight line.

The stability of the membrane was investigated in acidic, basic and neutral media, the results of which are listed in the Table below. Small specimens of the membrane were placed in contact with a number of aqueous solutions of varying pH at room temperature and the time required for the complete disappearance of the membrane was noted. The membrane was generally found to be more stable in weakly acidic media and extremely unstable in alkaline media.

TABLE 1

| SOLUTION | TIME REQUIRED FOR DISAPPEARANCE |
| --- | --- |
| 1 N HCL | 5 to 8 days |
| 0.1 N HCL | No change in 8 days |
| 0.01 N HCL | No change in 8 days |
| Deionized water | No change in 8 days |
| Borate (pH = 9) | 5 to 8 days |
| 0.01 N NaOH | Less than 5 hours |
| 0.1 N NaOH | Less than 5 hours |
| 1 N NaOH | Less than 1 hour |

To test the stability under physiological conditions, an accelerated stability study was performed in which samples of membrane were exposed to phosphate buffer of pH 7.4 at 60 deg C. Under these conditions, the membrane lost weight at the rate of about 1 percent per hour. After 60 hours, the membrane disintegrated and became soluble in the buffer.

EXAMPLE 11

Preparation of Poly(PEG-Lys) Membranes Cross-Linked with Tris(Aminoethyl)Amine

In a 100 mL beaker, 1.87 g of the PEG bis(succinimidyl carbonate) of Example 1 was dissolved in 20 ml of methylene chloride. In another beaker, 82 microliters (89 mg) of tris(aminoethylamine) was dissolved in 20 ml of methylene chloride. The triamine solution was added to the PEG solution with vigorous stirring. After about five minutes, films were cast of the solution following the procedure described above with respect to Example 16.

Swelling measurements of the membrane were made by the two methods described above with respect to Example 16. Both methods indicated that the membrane absorbed about six times its weight of water.

The stability of the membrane was investigated in acidic, basic and neutral media as described above. In sodium hydroxide (0.01 and 0.1N) the membrane disintegrated within a few hours. In acidic media and in phosphate buffer (pH 7.4) the membrane appeared to be stable for longer periods of time. The accelerated degradation study of Example 10 was also performed, in which the membrane remained intact for more than a week. An analysis of the buffer in which the accelerated stability study was conducted revealed that during the first 24 hours a small amount of PEG chains had leached from: the crosslinked membrane, but throughout the following 72 hours, no more PEG was leached.

EXAMPLE 12

Preparation of Poly(Caprolactone) Semi-IPN's of Poly(PEG-Lys) Membranes Cross-Linked by Diisocyanate The poly(PEG-Lys) membrane cross-linked by diisocyanatohexane was prepared as in Example 10, using 210 mg of the poly(PEG-Lys) of Example 5 having acyl hydrazine functional groups, dissolved in 10 mL of methylene chloride. The free base was formed with sodium bicarbonate, and the solution was then filtered. Prior to the addition of four microliters (3.9 mg) of the hexamethylene diisocyanate, 0.47 g of poly(caprolactone) (Union Carbide) (mw 72,000) was added to the filtrate, which was stirred for 30 minutes to dissolve the polymer completely. The poly(PEG-Lys) was cross-linked and films were cast following the procedure described above with respect to Example 16. The resulting membrane was hydrophilic and absorbed water with an equilibrium water content of 36%, whereas films made of poly(caprolactone) alone is hydrophobic.

EXAMPLE 13

A. Poly(cis-N-Pal-Hyp ester)

A poly(cis-N-Pal-Hyp) ester was prepared by melt transesterification of cis-4-hydroxy-N-palmitoyl-L-proline methyl ester (3) in the presence of aluminum isopropoxide (1% w/w), following a method described in J. Am. Chem. Soc. 109:817 (1987) for the polyesterification of N-protected trans-hydroxy-L-proline (Scheme 1). The monomer (3) was prepared from cis-hydroxy-L-proline(6) by conventional methods or from trans-N-Pal-Hyp (1) by reaction with triphenylphosphine (TPP) and diethyl azodicarboxylate (DEAD), via the bicyclic lactone(2) as described by Papaioannu et al. in Acta. Chem. Scand. 44:243 (1990).

B. Poly(ethylene glycol)-cis-Hyp conjugates (12) and (13)

Cis-N-Boc-L-proline methyl ester (10) was esterified with the succinic ester of momomethoxy-PEG (8) in presence of DCC/dimethylaminopyridine (DMAP), followed by deprotection of the cis-Hyp-N-terminus with a 4N HCl/dioxane solution to yield the conjugate (12) (Scheme 2a). Conjugate (13) was prepared by reaction of the succinimidyl carbonate activated monomethoxy PEG (9) with the lactone (11), followed by hydrolysis of the lactone in 2N KOH (Scheme 2b). Lactone (11) was prepared from trans-N-Boc-Hyp as described for compound 2 (Scheme 1), followed by deprotection of the N-terminus with 4N HCl/dioxane.

C. Poly(PEG-Lys-cis-Hyp) copolymers (16) and (17)

Were prepared by covalent attachment of the Hyp derivatives (10) and (11) to the pendant side chains of poly(PEG-Lys) as described for the PEG conjugates (12) and (13) (Scheme 3a and 3b). The extent of cis-Hyp attachment to the poly(PEG-Lys) copolymer was assessed by the ratio of Lys to Hyp as determined by amino acid analysis.

D. Polyethylene Qlycol-cHyp conjugated 1:2 Ratio

Polyethylene glycol may be conjugated with cHyp according to the following reaction scheme, resulting in a conjugate containing two cHyp moieties. As shown in the reaction pathway on the left, the cHyp hydroxyl groups may be reacted with a conjugate of PEG and succinic acid, thus forming multiple ester linkages. The cHyp carboxylic acid group can be protected with a methoxy group or another suitable protecting group.

In the reaction scheme on the right, the PEG is linked to two cHyp moieties through urethane linkages.

curve obtained from mixtures of known compositions, facilitated a quantitative analysis of the hydrolysis mixtures (Table A).

TABLE 2

EFFECT OF POLYMERIZATION CONDITIONS

| T (°C.) | Time (h) | Mw | Mn | cis/trans ratio |
|---|---|---|---|---|
| 180 | 17 | * | * | 9/1 |
| 195 | 5 | 21,590 | 15,856 | 3/1 |
| 210 | 17 | 14,224 | 10,166 | 1.8/1 |
| 210 | 5 | 15,644 | 11,377 | not determined |

*Mw and Mn could not be determined due to the high polydispersity of the sample

Since increasing the reaction temperature favored the undesirable formation of trans-Hyp, reaction conditions were optimized at 180° C. Polymers of very low molecular weight were obtained. At 210° C., polymers with a low

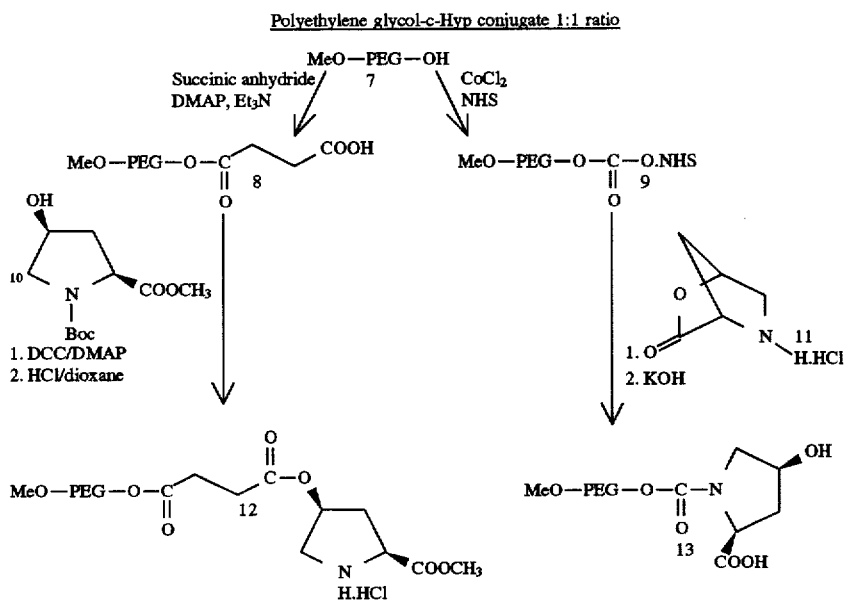

RESULTS

Poly(cis-4-hydroxy-N-palmitoyl-L-proline ester)

Since only the cis isomer of Hyp is pharmacologically active, the polymerization conditions were analyzed for effects on the retention of the cis configuration. The polymerization reaction was performed at temperatures ranging from 180° to 210° C. Polymers of highest molecular weight (Mw=21,600, Mn=15,900) were obtained when the reaction was conducted at 195° C. for 5 h. All polymers were then hydrolyzed in 1M NaOH and the conformation of Hyp formed during hydrolysis was determined by $^{13}C$ NMR.

A comparative hydrolysis of poly(trans-N-Pal-Hyp ester) obtained by the same method at 180° C. from trans-N-Hyp-Me showed that only trans-Hyp was formed. In contrast, hydrolysis of the polyesters obtained from the cis monomer led to mixtures of cis and trans isomers, which could be resolved due to a chemical shift difference of almost 1 ppm between the pyrrol ring carbons of the two isomers. Comparing the peak heights of 13C NMR spectra to a calibration cis/trans ratio were formed. However at 195° C., it was possible to prepare relatively high polymers which consisted predominately of cHyp.

Alternatively, a ring opening polymerization reaction can be run using the bicyclic lactone (2). The polymerization reaction was performed at 140° C. for variable periods of time (15 h to 5 days), using aluminum isopropoxide as the catalyst. This procedure gave low molecular weight polymers that consisted of an almost equimolar mixture of cis and trans-N-Pal-Hyp (cis/trans ratio: 0.9/1). Attempts to synthesize the target polymer using a coupling agents, such as DCC, in a direct coupling reaction failed due to the formation of the bicyclic lactone (2), via intramolecular esterification.

EXAMPLE 14

Attachment of CIS-HYP to Poly(Ethylene Glycol) Derivatives

Due to their physicochemical and biological properties, poly(ethylene glycols) (PEGs) are promising drug carriers.

Attachment of PEG to proteins was found to increase blood circulation time of the PET-protein conjugates and to delay clearance by the RES.

The attachment of cis-Hyp has been attached to two different poly(ethylene glycol) based carriers. In the first case, cis-Hyp was attached to a monomethoxy-PEG (Mw= 5,000) unit leading to new cis-Hyp conjugates having a 1:1 ratio of PEG to cis-Hyp (Scheme 2a and 2b). In a similar fashion cis-Hyp was attached to poly(PEG-Lys), a new polymeric drug carrier. In poly(PEG-Lys), PEG chains and L-lysine are connected via urethane bonds in a strictly alternating fashion. The carboxylic groups of the lysyl residue provide convenient anchors for the attachment of the pendant ligands. c-Hyp was bound to the PEG based carrier by labile ester bonds (Scheme 3a) and by more stable amide bonds (Scheme 3b).

EXAMPLE 15

Liposome Encapsulation

The encapsulation of the antifibrotic monomers and polymers of the present invention into liposomes may proceed in accordance with known techniques. An example of the preparation of the liposome encapsulated proline analogue of the invention follows: Small unilamellar liposomes were prepared by reverse phase evaporation using the method of Szoka and Papahadjopoulos as modified by Turrens and associates. A stock solution containing 97.5 mg L-alpha-dipalmitoyl lecithin, 24.2 mg cholesterol, and 9.6 mg stearylamine in a 14:7:4 molar ratio was dissolved in 5 ml of chloroform in a 50 ml round bottom flask. To this mixture, 50 mg of cHyp dissolved in 2.5 ml of 10 mM phosphate-buffered saline (PBS), pH 7.4, was added. The mixture was sonicated (model W-385 Ultrasonic Processor, Heat Systems-Ultrasonics, Inc., Farmingdale, N.Y.) at a power output of 7 for 1 min at 10° C. The mixture was converted to a homogeneous milky emulsion which was slightly viscous. The emulsion was transferred to a 50 ml rotary evaporation flask and volume was reduced under vacuum (400 torr) while maintaining the temperature at 25° C. When the emulsion became viscous and did not pool in the flask, 1.25 ml PBS was added. The evaporation was continued at 49° C. until the odor of chloroform was no longer detected and a free flowing turbid suspension was present. The suspension was kept at 4° C. overnight, centrifuged at 100,000×g for 35 min at 4° C., and recentrifuged after suspending the pellet in 6.5 ml of PBS. Prior to injection, the pellet was stored at 4° C. in 2.5 ml of PBS (40 µmol phospholipid/ml), filtered (0.22 µm Nalgene filter), and then passes serially through 18, 25 and 30 gauge needles.

The size profile of each batch of liposomes was determined by a fluorescent activated cell sorter (Coulter Epic 753 Dye Laser System, Coulter Electronics, Hialeah, Fa.) from linear and logarithmic forward angle light scattered signals at 488 nm at 1000 mwatts. Latex beads (0.1, 0.22 and 0.51µ in diameter) were used as size markers and approximately 20,000 signals were acquired per measurement. Since the charge, size and structure of L-proline is similar to that of cHyp, encapsulation efficiency of cHyp was estimated from the percent entrapment of 10 µCi of [$^{14}$C]-L-proline into the liposome pellet following centrifugation.

EXAMPLE 16

Liposome Encapsulated cHYP Administration

In this example, the liposome encapsulated antifibrotic agent of the invention was tested and compared with alternative formulations and modes of administration of the same antifibrotic agent. Accordingly, the proline analogue cis-4-hydroxy-L-proline (cHyp) entrapped in liposomes was administered to rats developing hypoxic pulmonary hypertension.

Methods

Materials

Materials were α-a-dipalmitoylphosphatidylcholine (780 g/mol) (Avanti Polar Lipids, Birmingham, Ala.), cholesterol (386.6 g/mol) and stearylamine (269.5 g/mol) (Sigma Chemical Co., St. Louis, Mo.), cis-4-hydroxy-L-proline (cHyp) (Calbiochem Corp., La Jolla, Calif.), [$^{14}$C]-L-proline (260 mCi/mM) and methanol and quaternary ammonium hydroxide (Protosol, New England Nuclear Co., Boston, Mass.), fluorescent latex microspheres (Fluoresbrite, Polysciences, Inc., Warrington, Pa.), 1,1', dioctadecyl-3,3,3', 3'-tetra-methylindorbocyanine perchlorate (D282, Molecular Probes, Inc., Eugene, Oreg.), and rabbit anti-factor VIII antibody and FITC goat-anti-rabbit antibody (Calbiochem Corp., La Jolla, Calif.). Chemicals were analytical grade.

Animals

Six week old male Sprague Dawley rats (Crl:CD[SD]BR) weighing 185–205 g and 8 week old female Swiss mice (Crl:CP-1[ICR]BR) weighing 30–32 g (Charles River Breading Laboratories, Wilmington, Mass.) were maintained in a holding area one week prior to study and were fed food and water ad libitum. Rats were randomly allocated to hypoxia or air groups; mice breathed air. Animals were kept in a 12-hour light-dark cycle.

Exposure Conditions

Four rats were placed in a polycarbonate chamber measuring 51×41×22 cm, and humidified gas (10% $O_2$, 90% $N_2$ flowed into the chamber at a rate of 400 ml/min. Gas samples were analyzed electrometrically (model MB53MK2, Radiometer, Copenhagen, Denmark); $PO_2$ ranged from 74–80 mmHg and $PCO_2$ from 3–5 mmHg. Air-breathing rats were kept in cages in the same room and were pair-fed to hypoxic animals by weighing the food consumed by hypoxic animals and feeding the same amount of food to air-breathing animals to ensure that final body weights were similar. The chambers were opened once daily for 10 min. to clean, weigh and feed the animals.

Hemodynamic Measurements and Heart Weight

A catheter was placed in the right ventricle of anesthetized rats (50 mg/kg pentobarbital intraperitoneally), and mean right ventricular pressure was measured using a pressure transducer (model P23Db, Statham, Instruments, Oxnard, Calif.) and recorded (model SP-2006, Statham Instruments). Pressure was measured after the animal had breathed air for 20 min. to eliminate the tonic response to hypoxia. After sacrifice by abdominal aorta transection, hematocrit and ratio of ventricular weights were measured, and the position of the catheter was confirmed at autopsy.

Biochemistry

Main pulmonary artery (9 mm in length) was excised and analyzed for total protein and hydroxyproline contents as previously described. Tissue was hydrolyzed in 6N HCl at 18° C. for 48 hrs., diluted 1:10 in water, and a 0.1 ml aliquot was assayed for total protein by the ninhydrin method using leucine as standard and for hydroxyproline by a colorimetric method. Results of triplicate measurements were expressed as content per vessel.

Preparation of Liposome

Unilamellar, positively charged phospholipid vesicles (liposomes) were prepared by reverse phase evaporation as previously described, except that the olecithin component was replaced with 97.5 mg L-α-dipalmitoylphosphatidylcholine.

Characterization of Liposomes

Liposome diameter was estimated by a single beam fluorescent activated cell sorter (Epic 752 Dye Laser System, Coulter Electronics, Hialeah, Fa.) using an argon ion laser emitting a 488 nm (1 watt). Latex microspheres (0.10–0.51 μm diameter) were used as size markers. Liposomes or microspheres were suspended in PBS, and size histograms were analyzed using a computer system (Easy 88 Epinet, Coulter Electronics) interfaced with the fluorescent activated cell sorter. The diameter of 90% of the liposomes ranged between 0.10 to 0.22 μm. Entrapment efficiency of cHyp into liposomes was estimated by substituting 10 μCi [$^{14}$C]-L-proline in place of cHyp (see above). A 0.1 ml aliquot of the [$^{14}$C]-L-proline entrapped liposome was added to 5 ml scintillation fluid (Liquiscint, National Diagnostics, Somerville, N.J.) and counted at 94% efficiency using a liquid scintillation counter (Tri-Carb, Packard Instruments, Downers Grove, Ill.). Percent encapsulation was estimated as the percentage of counts in liposomes and was found to be 51±6% (n=11) and remained constant during storage at 4° C. for 21 days.

Injections

Cis-4-hydroxy-L-proline dissolved in saline (free cHyp) or saline alone were injected subcutaneously (0.5 ml) or intravenously. Intravenous injections were performed in anesthetized animals (25 mg/kg thiopental, intraperitoneally). In rats, liposomes containing cHyp or empty liposomes were injected intravenously (18 mmol phospholipid in ~0.5 ml) via the dorsal vein of the penis over 5 sec using a 30 gauge needle. In mike, liposomes (18 μmol phospholipid in 0.5 ml) were injected, into the tail vein.

Mode of Delivery and Dose of cHyp

Four modes of delivery of cHyp were used in rats. Free cHyp (200 or 100 mg/kg) was injected subcutaneously twice daily during exposure to hypoxia. A single dose of free cHyp (200 mg/kg) was given intravenously prior to exposure to hypoxia.

Single doses of cHyp entrapped in liposomes (200 or 100 mg/kg) were injected intravenously prior to exposure to hypoxia.

Multiple doses of cHyp in liposomes (200 mg/kg) were injected intravenously prior to hypoxia and every 5 days during exposure to hypoxia.

Single doses of cHyp entrapped in liposomes after reticuloendothelial blockage were produced by intravenous injection of a single dose of empty liposomes followed 30 minutes later by a single intravenous dose of cHyp entrapped in liposomes (100 or 50 mg/kg) prior to exposure to hypoxia.

The purpose was to enhance the localization of liposomes containing cHyp to the lungs by prior treatment with empty liposomes as temporary reticuloendothelial blocking agents.

General Protocol

In each animal, we assessed the effect of injection of cHyp on five parameters of exposure to hypoxia: mean right ventricular pressure (RVP) measured after the animal had been removed from the hypoxic environment, ratio of ventricular weights (RV/[LV+S]), hematocrit, and the contents of hydroxyproline and protein in the pulmonary artery. For each experimental group, comparisons were made to a group exposed to hypoxia and injected with a control substance and to a group exposed to air. For free cHyp, the control substance was saline; for cHyp entrapped in liposomes, the control substance was empty liposomes. Groups were age-matched; the air group was weight-matched to the hypoxic group injected with the control substance. Average results of each parameter were compared.

Experimental Protocols

Twelve groups of rats were exposed to hypoxia and injected with cHyp (Groups 1–12, Table 1). Three groups were exposed to air and injected with cHyp (Groups 13–15, Table 1).

Groups were used to compare the mode of delivery of cHyp, various doses using the same mode of delivery, and the duration of effect of single or multiple injections of cHyp. Six experimental protocols were used.

The first protocol studied whether cHyp delivered in liposomes was more effective than free cHyp in preventing pulmonary hypertension. Efficacy for each mode of drug delivery was determined as the minimal dose of cHyp required to prevent pulmonary hypertension after 3 days exposure to hypoxia. Free cHyp was given as 200 or 100 mg/kg subcutaneously twice daily (Groups 1 and 2). Free cHyp was also given as a single dose of 200 mg/kg intravenously prior to hypoxia (Group 3). Groups 1–3 were compared to groups exposed to air and hypoxia for 3 days and injected subcutaneously twice daily with saline. Groups 1 and 2 were also compared to groups given liposome-entrapped cHyp as a single intravenous injection of 200 or 100 mg/kg prior to exposure to hypoxia (Groups 4 and 5). Groups 4 and 5 were compared to a group exposed to hypoxia for 3 days and given a single intravenous injection of empty liposomes prior to hypoxia.

The second protocol studied the duration of antihypertensive effect of a single dose of 200 mg/kg cHyp entrapped in liposomes injected prior to exposure to hypoxia. Groups were studied after 3, 5 or 7 days of exposure to hypoxia (Groups 4, 6 and 7). Results were compared to age-matched air groups and groups injected with single doses of empty liposomes after 3, 5 or 7 days exposure to hypoxia.

The third protocol studied whether 200 mg/kg cHyp entrapped in liposome injected intravenously prior to and every 5 days during exposure to hypoxia prevented pulmonary hypertension on day 21 (Group 8). Results were compared to a group exposed to air for 21 days and to a group injected with empty liposomes prior to and every 5 days during a 21-day exposure to hypoxia.

The fourth protocol studied whether reticuloendothelial blockade prior to injection of cHyp entrapped in liposomes improved drug action. Reticuloendothelial blockade was produced by a single intravenous injection of empty liposomes (18 μmol phospholipid in 0.5 ml) 30 min. prior to the injection of cHyp in liposomes. Groups given 100 or 50 mg/kg cHyp intravenously after reticuloendothelial blockade (Groups 9 and 10) were compared to an air group and to a hypoxic group injected with 100 mg/kg cHyp without reticuloendothelial blockade (Group 5). Groups were compared at 3 days after exposure to hypoxia.

The fifth protocol compared the duration of effect of a single dose of 100 mg/kg cHyp entrapped in liposomes after reticuloendothelial blockade and studied at 3, 5 and 7 days of hypoxia (Groups 9, 11 and 12). Results were compared to an air group and to groups with reticuloendothelial blockade injected with single doses of empty liposomes and studied on days 3, 5 and 7 of hypoxia.

The sixth protocol studied whether cHyp injected in air breathing rats affected any of the parameters of exposure to hypoxia. Air groups were given free cHyp 200 or 100 mg/kg subcutaneously twice daily for 3 days (Groups 13 and 14) and were compared to saline injected animals. A group was injected with 200 mg/kg of cHyp in liposomes every 5 days during a 21-day exposure to air (Group 15), and results were compared to a group injected with empty liposomes every 5 days during a 21-day exposure to air.

Effect of Acute Injection of Liposomes on Right Ventricular Pressure

One group of anesthetized, catheterized, air-breathing rats was injected with a bolus of liposomes to determine the acute pressor effect of liposomes. After RVP was stable for 5–10 min., a bolus of empty liposomes (18 μmol phospholipid in 0.5 ml) was injected via the dorsal vein of the penis, and blood pressure was recorded continuously until it returned to baseline. The maximal increase in RVP during the first 2 min. after injection was compared to the blood pressure during the period prior to injection.

Uptake of Radiolabelled Liposomes by Pulmonary Artery Endothelial Cells in Culture Fresh bovine pulmonary arteries were perfused with sterile PBS containing 0.1 mg/ml gentamicin, 37° C., until free of blood. The endothelial cells were mechanically removed and placed in Medium 199 containing 10% fetal bovine serum, 5% calf serum, IU/ml penicillin, 100 μg/ml streptomycin, and 0.05 mg/ml gentamicin, pH 7.4, and not fed or moved for at least one week. Thereafter, dividing cultures were fed twice weekly and passaged 7 times using a 2:1 split. Endothelial cells were identified by their characteristic cobblestone appearance in culture and the presence of angiotensin converting enzyme and factor VIII-related antigen by immunofluorescence. Endothelial cells ($1 \times 10^5$) and 100 μl of the above medium were added to each 38 mm$^2$ well of a 96-well flat bottom plate (Microtest II, Falcon Plastics, Oxnard, Calif.). Aliquots of liposomes containing [$^{14}$C]-L-proline (0.1 μCi, 0.2 μmol phospholipid, 5 μl per well) were added to the cultured cells. Separate wells were used to measure uptake at intervals from 30 min. to 5 hr. After incubation, cells were washed 3 times with PBS, removed with 0.1M sodium hydroxide, and radioactivity in a 500 μl aliquot counted in a liquid scintillation counter. The percent uptake of liposomes was estimated as the percentage of total radioactivity added per well.

Localization of Fluorescent Dye Entrapped in Liposomes in Pulmonary Artery Endothelial Cells in Culture To study whether liposomes are taken up by endothelial cells, liposomes (0.8 μmol phospholipid, 20 μl per well) containing the lipophilic fluorescent dye D282 were added to endothelial cells in culture for 0, 30 min., 1, 2, 3 and 5 hr. The cells were washed three times with medium and viewed using a microscope equipped with a fluorescence attachment. Endothelial cells with addition of empty liposomes were evaluated for autofluorescence.

Organ Distribution of Radiolabelled Liposomes

We estimated the distribution and retention of liposomes in selected organs by injecting radiolabelled liposomes in air-breathing mice and measuring radioactivity in the organs at times after injection. Mice were injected with [$^{14}$C]-L-proline in liposomes ($2.2 \times 10^5$ dpm in 100 μl) over one sec via the tail vein using a 30 g needle. Animals were killed by cervical dislocation at 1, 2, 6, 24, 48 and 72 hr. after injection. The lungs, heart, liver, spleen and kidneys were removed, rinsed in saline, blotted dry and weighed. A portion of each organ (100 mg) was solubilized in 2 ml methanol and quaternary ammonium hydroxide for 24 hr at 60° C. in a shaking water bath. A 100 μl aliquot of the suspension was added to 5 ml scintillation fluid (Econofluor, New England Nuclear Co., Boston, Mass.) and 2 ml methanol and quaternary ammonium hydroxide and counted in triplicate in a liquid scintillation counter. Counts were corrected for quenching by each tissue, and results were expressed as percent of total injected dose in each organ.

Statistical Analysis

Mean±SEM from each group were obtained. Data were analyzed by one-way ANOVA followed by Duncan's post-hoc test. Non-parametric data (animal survival) were analyzed by a continuity adjusted Chi-square analysis with Yates' correction. A P value of 0.05 was considered significant.

Results

In General

Substantially lower doses of cHyp were effective in preventing pulmonary hypertension and collagen accumulation in pulmonary arteries when given intravenously in liposomes compared to subcutaneous administration of the free agent. Moreover, a single intravenous dose of cHyp entrapped in liposomes had a sustained effect on suppressing pulmonary hypertension. Delivery of an antifibrotic agent in liposomes improves drug action in the treatment of experimental pulmonary hypertension.

Animals

Survival was 128 of 130 (98%) in combined air groups and 165 of 192 (86%) in the combined hypoxic groups ($X^2$–5.8, P<0.05). Survival at 3 days of animals exposed to hypoxia and injected with saline or free cHyp was 13 of 16 (81%); survival of animals exposed to hypoxia and injected with liposomes was 51 of 61 (84%) (NS). After 3 days, 14 deaths occurred in the hypoxic group treated with liposomes (there were no age-matched saline or free cHyp treated animals exposed to hypoxia to compare survival). Initial body weight was 198±4 g (mean±SEM) (n=322); final body weights were: day 3, 190–202 g; day 5, 204–208 g; day 7, 202–208 g; and day 21, 225–230 g. We found no differences on any day in final body weights among hypoxic animals treated with cHyp, hypoxic animals treated with the test substance and air-breathing animals.

Hypoxia and Treatment with Emtpy Liposomes

Exposure to hypoxia from day 0 to day 21 produced progressive increases in all parameters in rats injected with empty liposomes; RVP increased from 9±1 to 21±2 mmHg, RV/(LV+S) from 0.24±0.01 to 0.43±0.02, hematocrit from 48±1 to 66±1%, hydroxyproline content from 74±4 to 163±14 μg/vessel and protein content from 1.2±0.1 to 3.2±0.3 mg/vessel (n=7–8, all P<0.05). All parameters were increased as early as 3 days exposure to hypoxia (Table 2).

Free vs. Liposome-Entrapped cHyp

The effect of free cHyp on preventing pulmonary hypertension at 3 days is shown in Table 2. Treatment with 200 mg/kg cHyp subcutaneously twice daily for 3 days produced reductions in all 5 parameters compared to the saline injected hypoxic group. However, the values were greater than those in the air group, indicating that free cHyp partially prevented pulmonary hypertension. Injection of 100 mg/kg free cHyp subcutaneously for 3 days did not prevent increased RVP, RV/(LV+S) or hydroxyproline or protein contents; there was partial decrease in hematocrit (Table 2). Free cHyp injected intravenously prior to hypoxic exposure had no effect on any parameter (Table 2). A single dose of 200 mg/kg cHyp entrapped in liposomes injected prior to exposure to hypoxia partially prevented increases in RVP and hematocrit and completely prevented increases in RV/(LV+S) and contents of hydroxyproline and protein in pulmonary arteries at 3 days (FIG. 1). A single intravenous dose of 100 mg/kg cHyp entrapped in liposomes had no protective effect on any of the parameters at 3 days.

Duration of a Single Dose of cHyp Entrapped in Liposomes

A single intravenous injection of 200 mg/kg cHyp prior to exposure to hypoxia partially or completely prevented increases in RVP, RV/(LV+S) and hydroxyproline content of pulmonary artery at 3 and 5 days; increases in hematocrit and protein content were prevented at 3 days but not at 5 days (FIG. 1). At 7 days, a single injection of 200 mg/kg cHyp in liposomes did not prevent increases in any of the measured parameters (FIG. 1). Thus, a single intravenous injection of 200 mg/kg cHyp in liposomes prior to exposure to hypoxia partially suppressed the development of pulmonary hypertension, right ventricular hypertrophy and pulmonary artery collagen accumulation for 5 days.

Intermittent Doses of cHyp Entrapped in Liposomes

Intermittent injections of cHyp in liposomes every 5 days during the 21 day exposure period partially prevented the increases in RVP, RV/(LV+S) and hydroxyproline and protein contents of pulmonary artery; there was no effect on hematocrit (Table 3). These results show that intermittent doses of single doses of cHyp in liposomes suppress the development of pulmonary hypertension for as long as three weeks.

Single Dose of cHyp Entrapped in Liposomes after Reticuloendothelial Blockade

Figure 3:
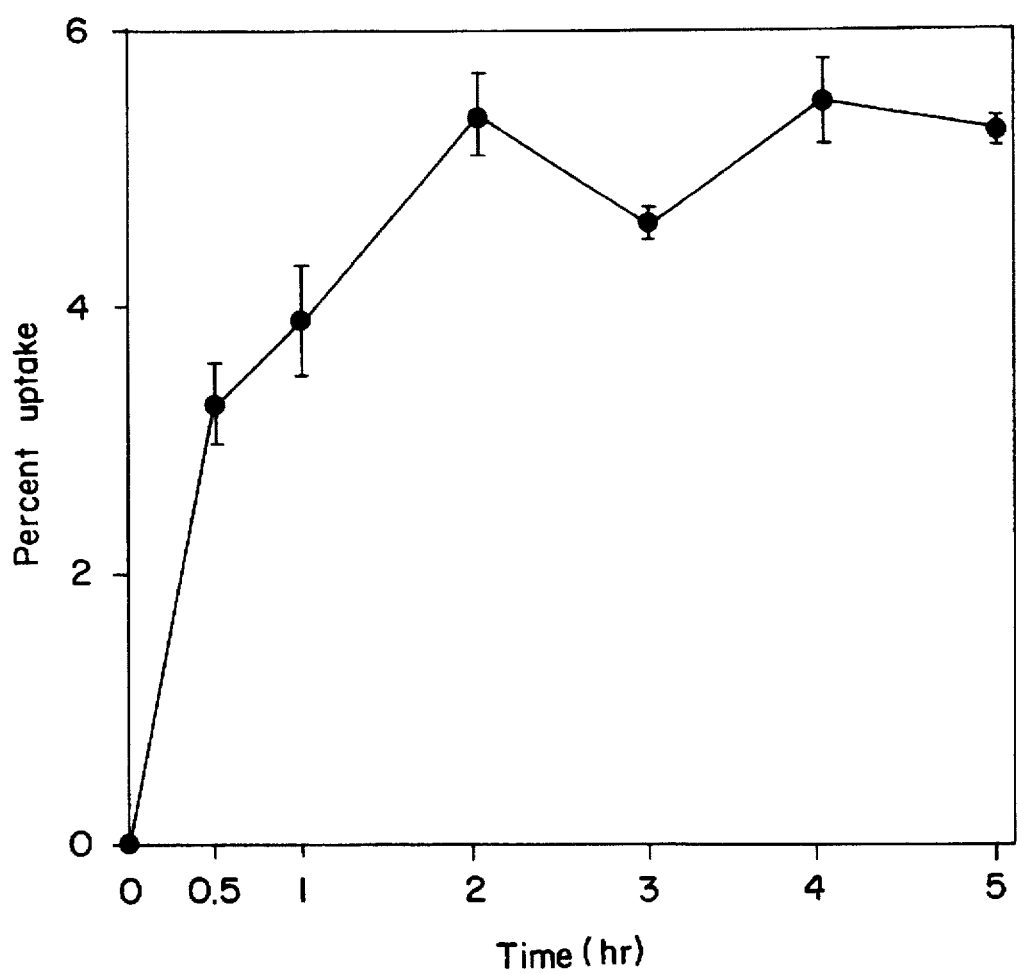
FIG. 3 is a graph depicting endothelial cell uptake of [$^{14}$C]-L-proline entrapped in liposomes. Data points, mean; bracket, ±SE; n=4. Time, time of study; percent, percent uptake of radiolabelled liposomes by cultured pulmonary artery endothelial cells.

In animals with reticuloendothelial blockade, a single dose of 100 mg/kg cHyp entrapped in liposomes partially prevented the increases in RVP, RV/(LV+S) and hydroxyproline content of the pulmonary artery at 3 days; there was no apparent effect on hematocrit and protein content of pulmonary artery at 3 days (FIG. 2). A dose of 50 mg/kg had no protective effect on any parameter at 3 days (FIG. 3). Since the minimal effective dose of cHyp in liposomes without reticuloendothelial blockade was 200 mg/kg, these results suggest that reticuloendothelial blockade prior to a single dose of cHyp in liposomes results in a lower effective dose of cHyp.

Duration of a Single Dose of cHyp Entrapped in Liposomes after Reticuloendothelial Blockade In animals with reticuloendothelial blockade, treatment with a single intravenous injection of 100 mg/kg prior to exposure to hypoxia partially or completely prevented increases in RVP, RV/(LV+S) and hydroxyproline content of the pulmonary artery at 3 and 5 days; there was no effect on hematocrit or protein content (FIG. 2). At 7 days after a single injection, the agent did not prevent increases in any of the measured parameters (FIG. 2). The pattern of suppression was similar to that found without reticuloendothelial blockade (FIG. 1), except the dose was 100 mg/kg instead of 200 mg/kg.

cHyp in Air-Breathing Rats

There was no effect of 200 mg/kg or 100 mg/kg cHyp injected twice daily subcutaneously for 3 days on any of the measured parameters (Table 2). Also, intermittent intravenous injections of 200 mg/kg cHyp in liposomes every 5 days during a 21-day air exposure period had no effect on any parameter (Table 3).

Effect of Injection of Liposomes on Right Ventricular Pressure

Mean right ventricular pressure increased from 9+1 to 11+1 (mmHg) (n=5) within 2 min after injection of cHyp entrapped in liposomes (P<0.05). Injection of saline under the same conditions had no effect on RVP (9+1 vs. 10+1 mmHg, n=4).

Uptake of Liposomes by Endothelial Cell in Culture

Percent uptake of liposome containing [$^{14}$C]-L-proline by pulmonary artery endothelial cells was 3.3±0.3% at 30 min. Uptake was maximal at 5.4±0.3% after 2 hr and remained at that level for 5 hr (FIG. 3).

Localization of Fluorescent Dye Entrapped in Liposomes

Figure 4:
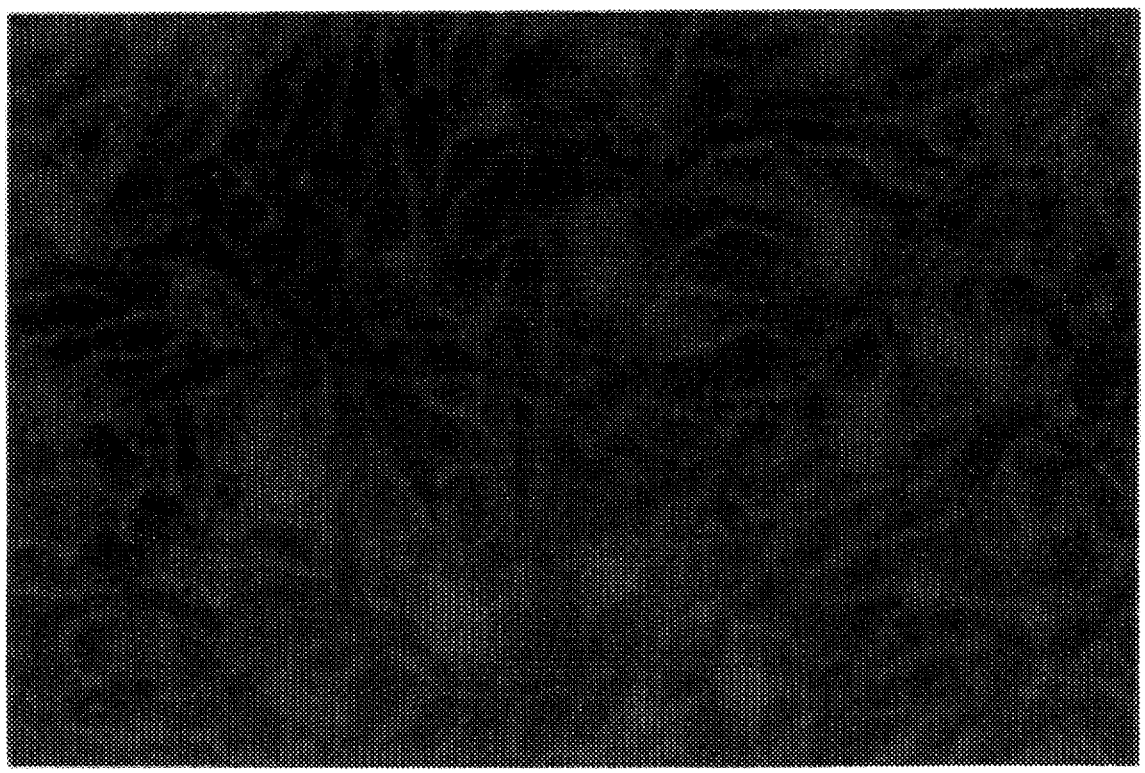
FIG. 4 shows the localization of fluorescent dye entrapped in liposomes in cultured pulmonary artery endothelial cells. Diffuse uptake of fluorescent dye by endothelial cells.

At 30 min after incubation with the fluorescent dye D282, a diffuse pattern of immunofluorescence was observed in endothelial cell membranes (FIG. 4). At 2 hr a few fluorescent intracellular vesicles appeared which became more abundant at 3 to 5 hr after incubation. Autofluorescence was absent in cells not incubated with D282.

Organ Distribution of Radiolabelled Liposomes

Figure 5:
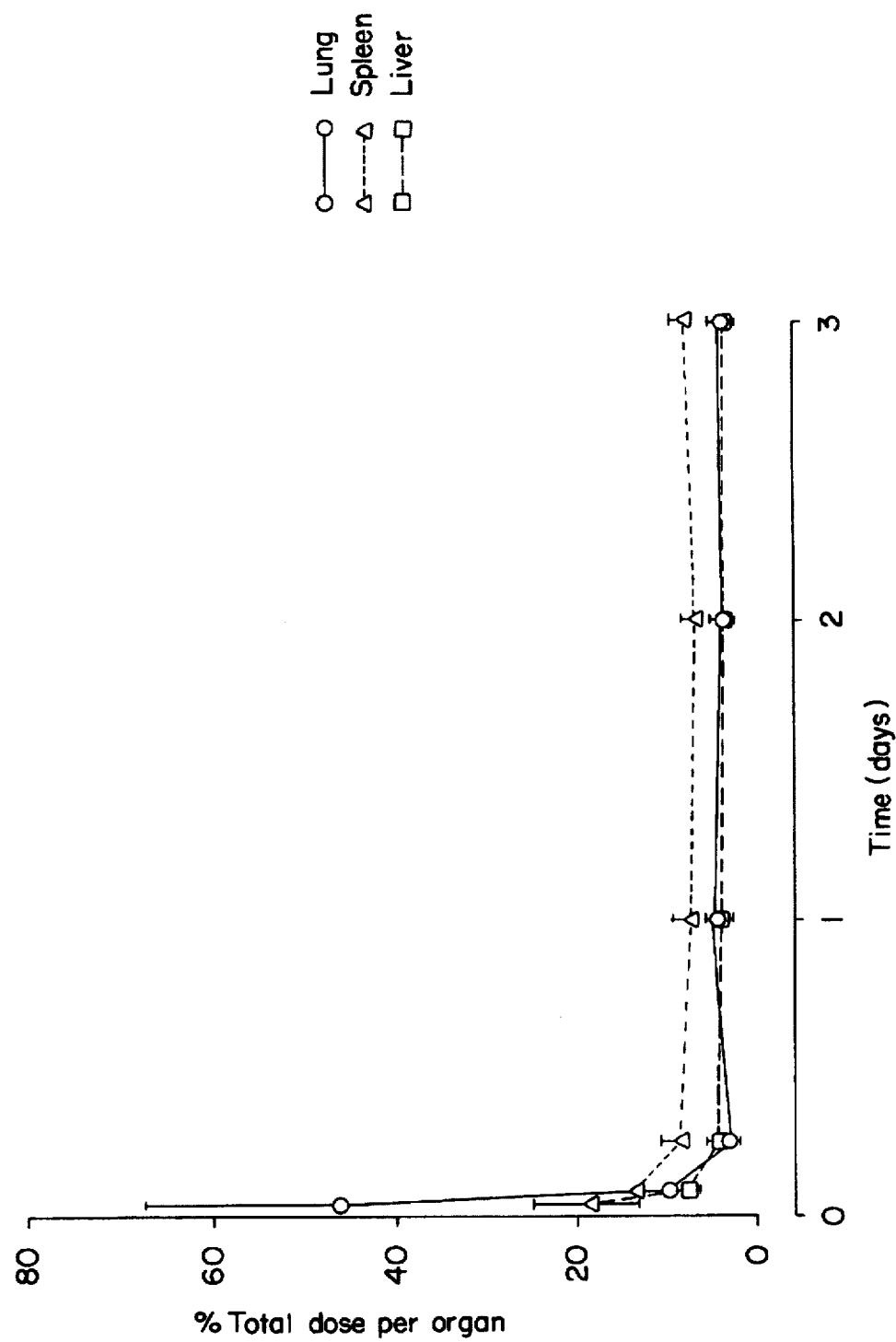
FIG. 5 is a graph depicting the uptake of [$^{14}$C]-L-proline in liposomes in selected organs. Percent of total injected dose of [$^{14}$C]-L-proline (ordinate) versus time after injection (abscissa). Data points, mean; bracket, ±SE, n=4.

Soon after administration of [$^{14}$C]-L-proline entrapped in liposomes, radioactivity appeared in the lung where it reached a maximum of 49±14% of total injected dose during the first 20 min (FIG. 5). There was a rapid decrease in lung activity reaching a value of 5±1% at 6 hr. Spleen took up a greater proportion of radioactivity (9±1% at 6 hr) and retained –7–9% for up to 72 hr. Liver retained about the same amount as lung; heart and kidney contained <2% activity after 6 hr (not shown). After 72 hr, the lung contained 5±1% of total activity (FIG. 5).

Discussion

The examples above demonstrate that the intravenous injection of cHyp in liposomes partially prevents the development of pulmonary hypertension in rats exposed to hypoxia. Liposome entrapment was necessary for drug action since intravenous injection of free cHyp was ineffective.

Compared to subcutaneous administration, intravenous delivery of cHyp in liposomes required considerably less total dose of drug to prevent hypertension. Moreover, delivery of cHyp in liposomes resulted in sustained drug effect; pulmonary hypertension was suppressed for 5 days after a single intravenous injection of cHyp in liposomes. This effect could be extended for as long as three weeks by a single injection every 5 days. Drug action on the pulmonary circulation could be improved by blocking uptake by reticuloendothelial organs prior to delivering the agent.

cHyp was chosen to test the effect of liposome delivery of drugs to blood vessels because it consistently prevents the early hemodynamic and biochemical changes of hypoxic pulmonary hypertension in the rat. The minimal total dose of cHyp required to prevent hypoxic pulmonary hypertension using different modes of delivery was compared.

At 5 days the results were as follows: subcutaneous, 400 mg/kg (200 mg/kg twice daily); single dose entrapped in liposomes without reticuloendothelial blockade, 200 mg/kg; single dose entrapped in liposomes with reticuloendothelial blockade, 100 mg/kg. Over the 5-day interval, the dose using cHyp entrapped in liposomes following reticuloendothelial blockade was approximately 20 times more effective than a subcutaneous dose of free cHyp.

The assumption is made that cHyp is released from liposomes in the vicinity of vascular cells synthesizing collagen, thereby preventing accumulation of collagen. There are two general pathways which liposomes might follow to enter the blood vessel wall. First, liposomes injected intravenously may be taken up by pulmonary vascular endothelial cells. Liposomes pass easily into reticuloendothelial organs because the endothelium of these organs is fenestrated. In organs with tight endothelium, such as lung, liposomes remain associated with endothelial surfaces until they are degraded or endocytosed. Although it was shown that liposomes are taken up by endothelial cells in vitro, there is no evidence that this process occurred in vivo. Second, liposomes may be taken up by circulating blood phagocytes and migrate into the lung tissue. Blood monocytes phagocytose liposomes and subsequently migrate to the alveoli to become alveolar macrophages. The analogue may be released from blood cells as they pass through the blood vessel walls. Liposomes are also phagocytosed by pulmonary intravascular macrophages, but the rat has few if any of these cells. Either of these two pathways may be involved in release of cHyp to blood vessel walls.

These biochemical mechanisms probably account for the decreased accumulation of collagen in pulmonary arteries in the Examples. In addition, collagen synthesis in main pulmonary arteries of rats is markedly increased within 3 days of exposure to hypoxia and remains elevated for 7 days. Collagen synthesis is increased only in the pulmonary artery, probably because hypoxia causes structural remodeling in response to hypoxic hypertension in the pulmonary circulation. Proline analogues impair collagen formation in tissues undergoing increased collagen synthesis, such as the pulmonary artery in early hypoxic pulmonary hypertension.

Treatment with cHyp is relatively specific for inhibiting collagen synthesis. For example, doses of cHyp which inhibit collagen accumulation do not affect elastin accumulation. Nevertheless, it was observed that treatment with cHyp prevented increases in total protein accumulation at 3 days. Suppression of protein accumulation cannot be accounted for by the decreased collagen since collagen synthesis contributes only about 4–5% of the total protein synthesis in hypertensive pulmonary arteries of rats. One explanation is that cHyp may have interfered with the ability of vascular smooth muscle cells and fibroblasts to proliferate, since cHyp inhibits proliferation of cultured cells by blocking collagen secretion required for cells to attach and grow. Marked cell proliferation occurs in hilar pulmonary arteries of rats 2–3 days after onset of hypoxia, and suppression of this proliferation by cHyp may explain why protein content was suppressed is early hypertension. At 5 days and later, there is little cell proliferation and cHyp has no effect on protein accumulation after 3 days.

Hypoxia-induced polycythemia was inhibited by the higher doses of cHyp, an effect previously noted with subcutaneous injection of cHyp.

The rate of rise of right ventricular pressure and hydroxyproline content were similar between 0 and 3 days in the hypoxic group and between 5 and 7-days in the hypoxic groups given a single injection of cHyp in liposomes (FIGS. 1 and 2). It was speculated that the suppressive effect of cHyp in liposomes diminished after 5 days, and collagen accumulated rapidly in the blood vessel wall. The late increase in collagen may have contributed to narrowing of the vascular lumen producing hypertension. The stimulus for rapid collagen accumulation at flow-resistive sites, presumably hypoxic vasoconstriction, persisted during hypoxia, but the added effect of collagen accumulation occurred only after the drug effect wore off.

It is possible to enhance the delivery of liposomes to the lung by blockade of the reticuloendothelial organs. With blockade, half as much cHyp is required in liposomes to prevent the rise in pulmonary blood pressure as without RES blockade, suggesting that blockade produced a shift toward a greater portion of injected liposomes to the lung.

Intravenously injected liposomes will be initially distributed to lungs since it is the first organ they contact. Thereafter, liposomes are distributed to other organs or are excreted. A small fraction of the total radioactivity (4–5%) remains in the lung for as long as 3 days, incorporated into tissue protein or retained in liposomes. These findings are consistent with the observation that cHyp within the lung is available to inhibit collagen accumulation for up to 5 days after intravenous injection.

In conclusion, the results show that intravenous injection of an agent entrapped in liposomes substantially improves the action of an agent which inhibits the development of hypertension, probably by delivering a locally high concentration of drug which is released over time within the blood vessel wall. The encapsulated agent given intravenously was approximately 20 times more effective than the unencapsulated agent given subcutaneously.

TABLE 3

| | | | EXPERIMENTAL GROUPS | | |
|---|---|---|---|---|---|
| Mode of Delivery of cHyp | Route | Dose (mg/kg) | Frequency of Injection Exposure to Hypoxia | Duration of Exposure (days) | Group Number |
| Free | sc | 200 | Twice daily during hypoxia | 3 | 1 |
| | sc | 100 | Twice daily during hypoxia | 3 | 2 |
| | iv | 200 | Single dose prior to hypoxia | 3 | 3 |
| Liposomes, single doses | iv | 200 | Single dose prior to hypoxia | 3 | 4 |
| | iv | 100 | Single dose prior to hypoxia | 3 | 5 |
| | iv | 200 | Single dose prior to hypoxia | 5 | 6 |
| | iv | 200 | Single dose prior to hypoxia | 7 | 7 |
| Liposomes, intermittent doses | iv | 200 | Prior to hypoxia & every 5 days during hypoxia | 21 | 8 |
| Liposomes, single doses, reticuloendothelial blockage | iv | 100 | Empty liposomes followed 30' later by single dose prior to hypoxia | 3 | 9 |
| | | 50 | | 3 | 10 |
| | iv | 100 | | 5 | 11 |
| | iv | 100 | | 7 | 12 |
| | | | Exposure to Air | | |
| Free | sc | 200 | Exposure twice daily during air | 3 | 13 |
| | sc | 100 | | 3 | 14 |
| Liposomes, single doses | iv | 200 | Every 5 days during exposure | 21 | 15 |

Abbreviations: cHyp, cis-4-hydroxy-L-proline; free, cHyp not contained in liposomes; liposomes, cHyp entrapped in liposomes; sc, subcutaneaus; iv, intravenous

TABLE 4

EFFECTS OF INJECTION OF FREE cHyp ON HEMODYNAMIC AND BIOCHEMICAL MEASUREMENTS ON 3 DAYS

| Exposure/Regimen | n | RVP (mmHg) | RV/(LV + S) (%) | Hct (%) | Hydroxyproline (mg/vessel) | Protein (mg/vessel) |
|---|---|---|---|---|---|---|
| Air, Saline | 6 | 9 ± 1 | 0.24 ± 0.01 | 48 ± 1 | 75 ± 4 | 1.2 ± 0.1 |
| Hypoxia, saline | 8 | 14 ± 1* | 0.30 ± 0.01 | 54 ± 1* | 90 ± 2* | 1.7 ± 0.1* |
| Hypoxia, free cHyp 200 mg/kg sc bid × 3 days | 10 | 10 ± 1** | 0.25 ± 0.01** | 51 ± 1** | 78 ± 4** | 1.4 ± 0.1** |
| 100 mg/kg sc bid × 3 days | 5 | 14 ± 1 | 0.31 ± 0.02 | 51 ± 1** | 94 ± 4 | 2.3 ± 0.3 |
| 200 mg/kg iv × 1 injection | 9 | 14 ± 1* | 0.32 ± 0.01* | 55 ± 1* | 88 ± 7* | 2.3 ± 0.3* |
| Air, free cHyp | | | | | | |
| 200 mg/kg sc bid × 3 days | 6 | 9 ± 1 | 0.24 ± 0.01 | 46 ± 1 | 72 ± 5 | 1.2 ± 0.1 |
| 100 mg/kg sc bid × 3 days | 4 | 9 ± 1 | 0.24 ± 0.01 | 47 ± 1 | 70 ± 2 | 1.2 ± 0.1 |

Values, mean ± SEM. Measurements taken 3 days after exposure to air on 10% $O_2$. n = number animals/group; cHyp, cis-4-hydroxy-L-proline; iv, intravenous; sc, subcutaneous; bid, twice daily; RVP, mean right ventricular pressure; RV/LV + S), ratio of ventricular weights; Hct, hematocrit; *, $P,0.05$ compared with hypoxia

TABLE 5

EFFECTS OF INTERMITTENT INJECTIONS OF cHyp IN LIPOSOMES ON HEMODYNAMIC AND BIOCHEMICAL MEASUREMENTS ON DAY 21

| Exposure/Regimen | n | RVP (mmHg) | RV/(LV + S) (%) | Hct (%) | Hydroxyproline (mg/vessel) | Protein (mg/vessel) |
|---|---|---|---|---|---|---|
| Air, empty liposome | 8 | 9 ± 1 | 0.24 ± 0.01 | 47 ± | 79 ± 6 | 1.5 ± 0.1 |
| Air, liposomes, cHyp | 8 | 9 ± 1* | 0.24 ± 0.01 | 46 ± 1 | 84 ± 3 | 1.4 ± 0.2 |
| Hypoxia, empty | 7 | 21 ± 2 | 0.43 ± 0.02* | 66 ± 1** | 163 ± 14* | 3.2 ± 0.3* |
| Hypoxia, liposomes, cHypo | 7 | 15 ± 1** | 0.36 ± 0.01** | 68 ± 1* | 121 ± 12** | 2.4 ± 0.2** |

Values, mean ± SEM. Measurements taken 3 days after exposure to air on 10% $O_2$. n = number animals/group; cHyp, cis-4-hydroxy-L-proline; bid, twice daily; RVP, mean right ventricular pressure; RV/LV + S), ratio of ventricular weights; Hct, hematocrit; *, $P,0.05$ compared with hypoxia Any of the antifibrotic agents other than cHyp can also be liposome encapsulated and administered to treat fibrotic conditions. Each of the antifibrotic agents can be administered in liposomes in an amount effective to treat diseases where collagen metabolism is of concern.

The antifibrotic agents can also be linked to a monomer and incorporated into lipsomes. For purposes of illustration, the antifibrotic agent below is cHyp linked to ethylene glycol.

cHyp-OCH$_2$CH$_2$—OH

The linkage could again be an ether, ester or another linkage. Also, an additional antifibrotic compound can be linked to the glycol through the hydroxyl group.

If ethylene glycol is used as the monomer, safety and toxicity may need to be taken into account. A preferred monomer in this regard would be propylene glycol or another suitably non-toxic monomer.

A polymeric form which can also be included herein is the polymer:

cHyp-PEG or cHyp-(PEG-cHyp)$_y$

The cHyp can be linked directly or through a linking compound. Also, the cHyp can be substituted in whole or in part with another antifibrotic agent. The variable Y in this case can be an integer from 1 up to about 100.

Figure 6:
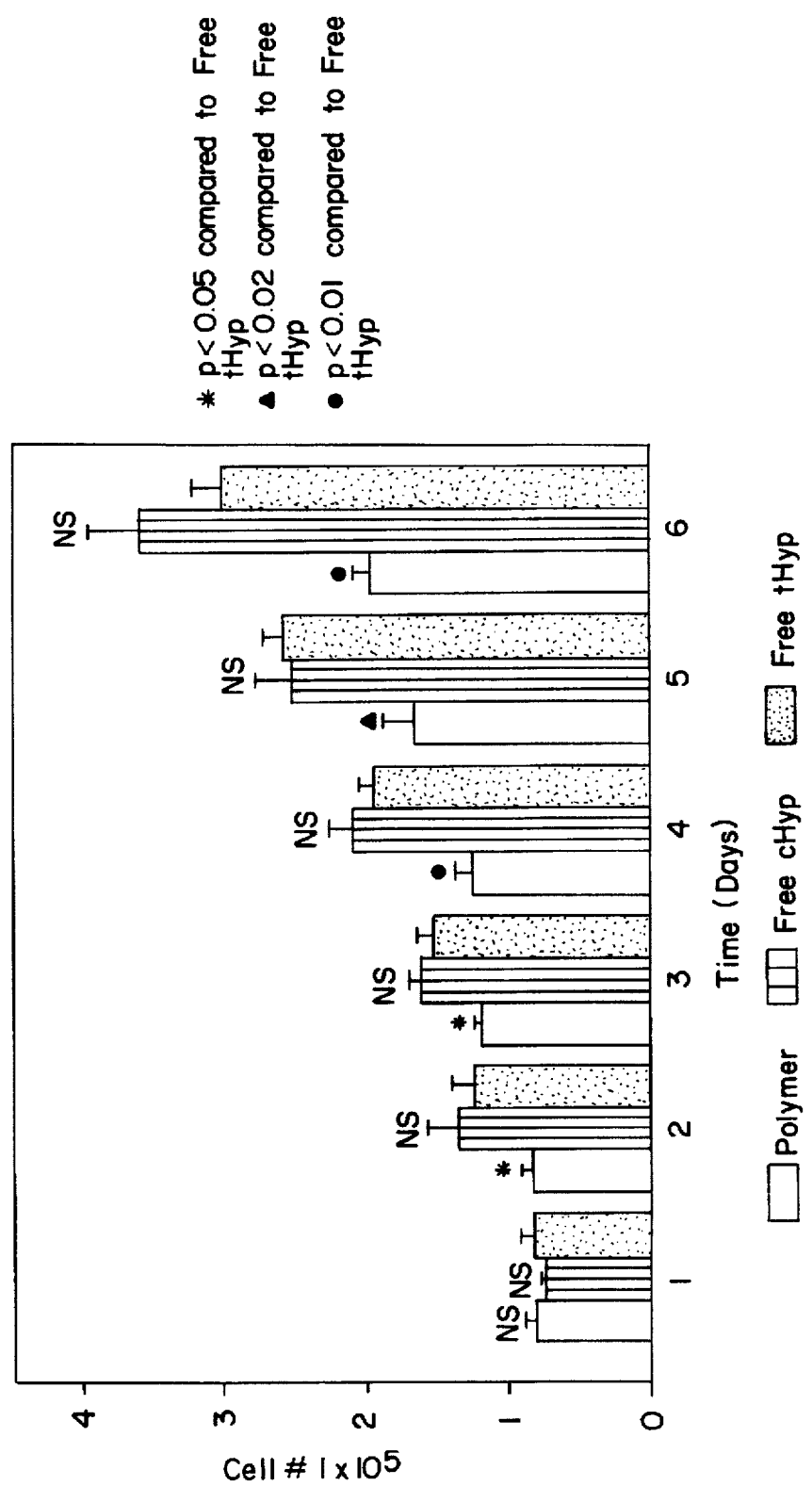
FIG. 6 is a graph of smooth muscle cell proliferation in the presence of polymeric polyethylene glycol (MW 2000) -lysine chemically reacted with cHYP via ester linkages.
Figure 7:
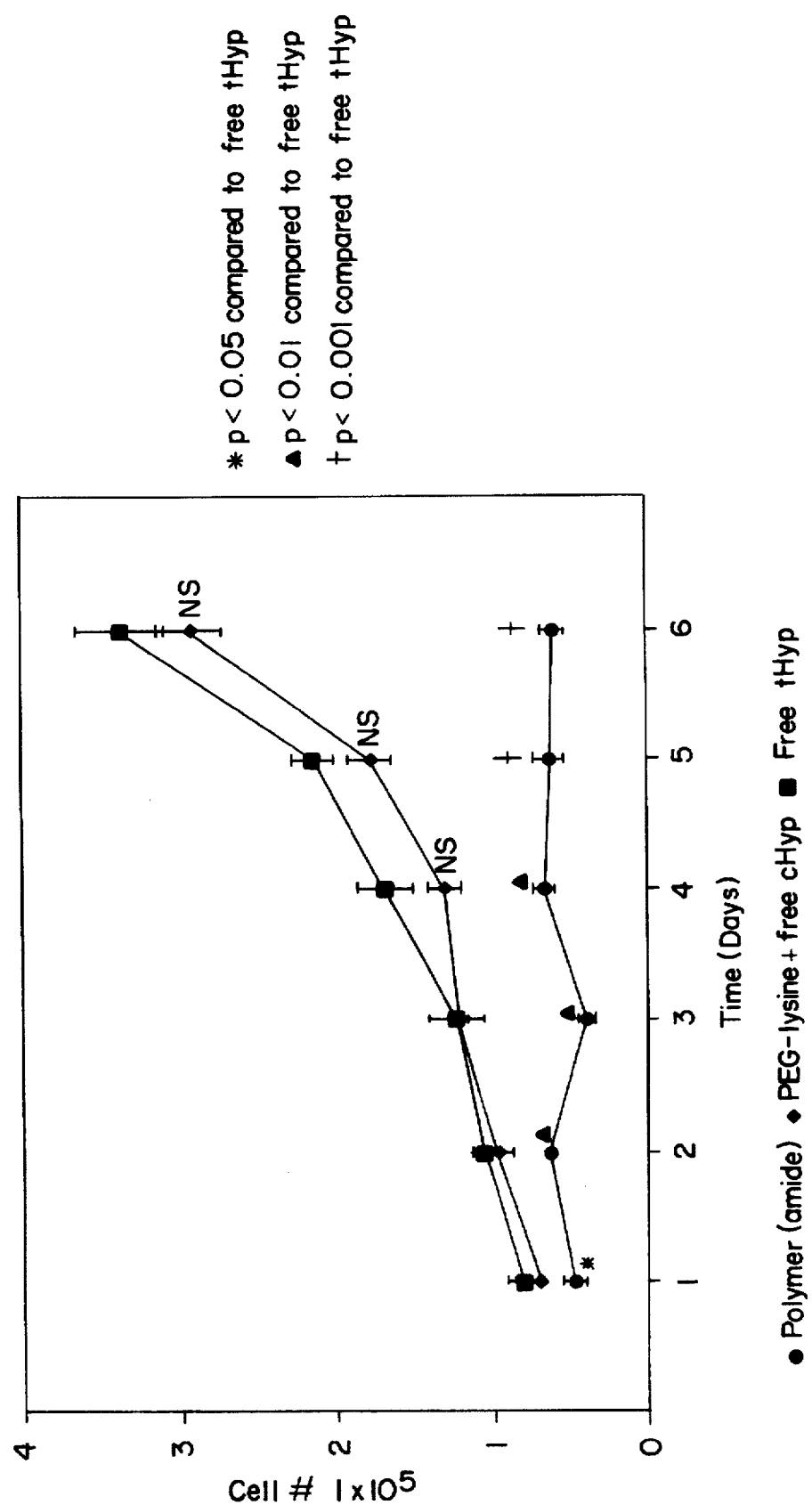
FIG. 7 is a graph of smooth muscle cell proliferation in the presence of polymeric polyethylene glycol (MW 2000) -lysine chemically reacted with cHYP via amide linkages.
Figure 8:
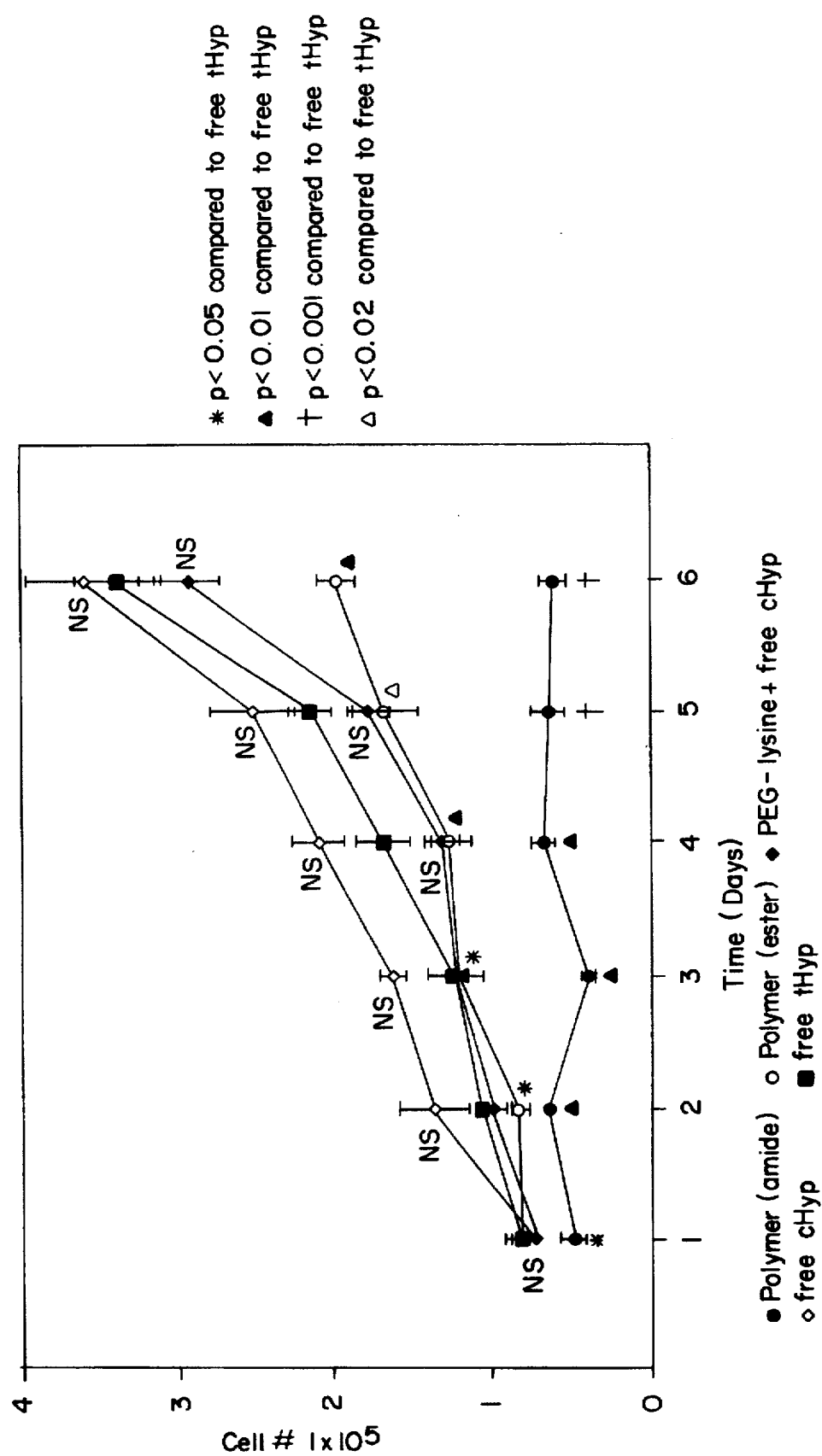
FIG. 8 is a comparison of the smooth muscle proliferation in the presence of ester linked cHYP and amide linked cHYP. Both polymeric forms are compared to PEG lysine and free cHYP, free cHYP and free tHYP, which is without substantial biological activity.
Figure 9:
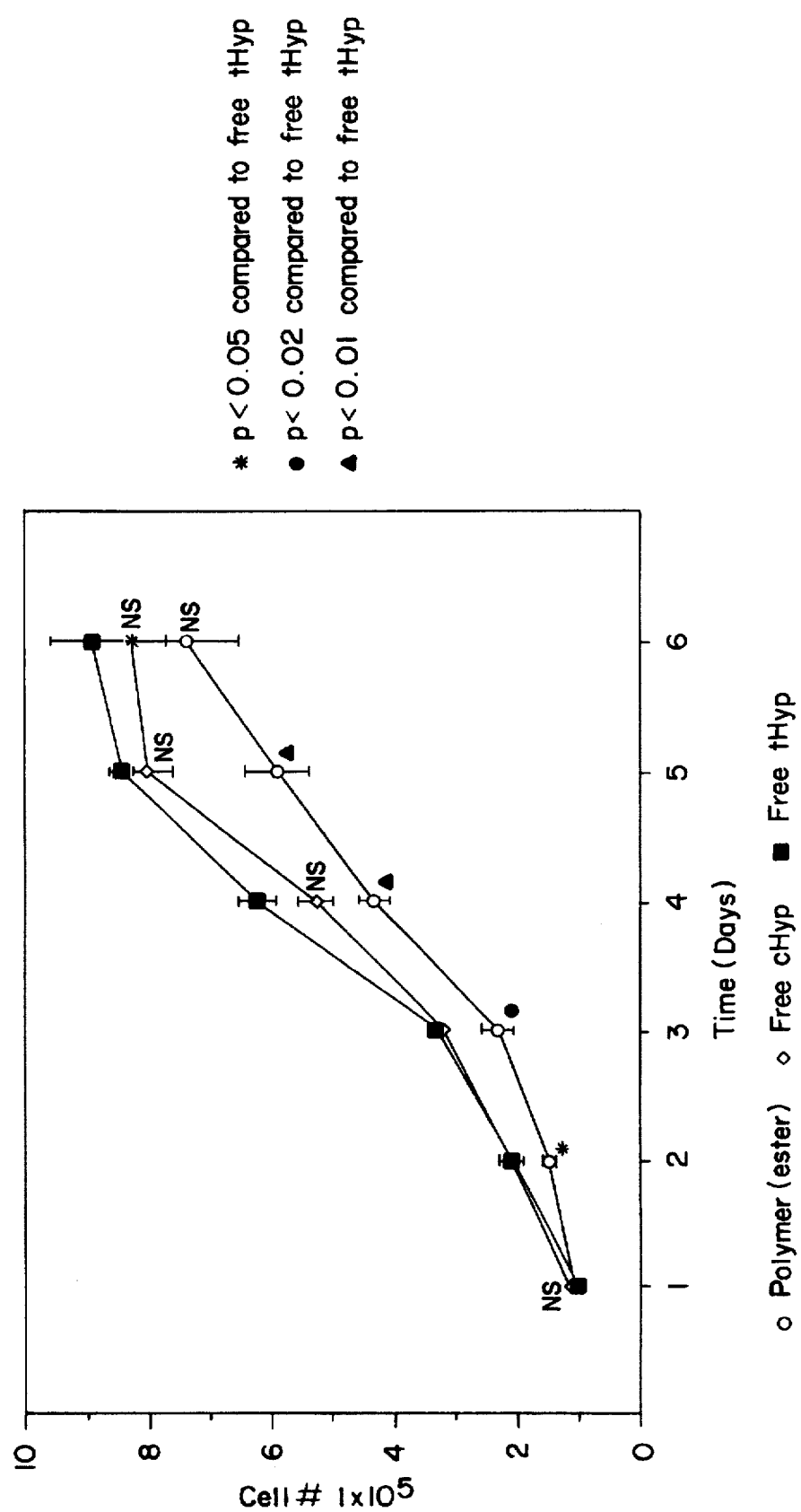
FIG. 9 is a graph of cell proliferation using rat lung fibroblasts in the presence of polyethylene glycol-lysine linked to cHYP via ester linkages.

As can be noted with respect to FIGS. 6 through 9, the antifibrotic agents can be conjugated with PEG or another polymer and used to reduce cellular proliferation in the presence collagen metabolism. In FIG. 6, the effect of free cHyp, polymeric cHyp and free trans hydroxyproline were compared over a six day period.

Smooth muscle cells were allowed to proliferate in the presence of free cHyp, polymeric cHyp and trans hydroxyproline. The polymeric cHyp was produced as described above and contained ester linkages. On each day, the cells were trypsinized and counted with a hemocytometer. Cellular proliferation was significantly reduced in the cHyp polymer group, as compared to the free cHyp and tHyp groups. This is further supported by the data represented in FIG. 9, generated with fibroblast cells.

When the polymer is conjugated with cHyp via amide linkages, cellular proliferation is further reduced. See, e.g., FIG. 7, which a comparison is presented between the ester linked polymer and the amide linked polymer in FIG. 8.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A polymeric compound comprising:
   A. a backbone which is a reaction product of:
      1. a poly(allcylene oxide); and
      2. a linking compound selected from the group consisting of lysine, arginine, ethanolamine, and succinic acid; and
   B. one or more side chains directly conjugated to said linking compound of said backbone comprising:
      an antifibrotic agent selected from the group consisting of: cis-4-hydroxy-L-proline; 3,4-dehydro-L-proline; cis-4-fluoro-L-proline; cis-4-chloro-L-proline; laevo and cis isomers of compounds of the general structural formula:

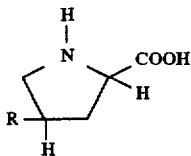

wherein R is OH, Cl, F, NH$_2$, SH, SCH$_3$, OCH$_3$, ONO$_2$, OSO$_2$, OSO$_3$H, H$_2$PO$_4$, or COOH; and pharmaceutically acceptable salts thereof.

2. A polymeric compound in accordance with claim 1 wherein said backbone comprises the reaction product of a polyethylene or polypropylene glycol, and lysine as said linking compound and said side chain antifibrotic agent directly conjugated to said linking compound is cis-hydroxyproline.

3. A polymeric compound in accordance with claim 2 wherein said backbone to which said side antifibrotic agent is directly conjugated has the following partial structure:

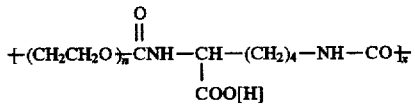

wherein n is an integer in the range of from about 20 to about 114 and x is an integer in the range of from about 10 to about 200.

4. A polymeric compound in accordance with claim 2 wherein said backbone comprises the reaction product of polyethylene glycol and lysine as said linking compound, and said side chain comprises cis-hydroxyproline.

5. A polymeric compound in accordance with claim 4 having ester linkages between said linking compound of said backbone and said cis-hydroxyproline side chain.

6. A polymeric compound in accordance with claim 4 having urethane linkages between said linking compound of said backbone and said cis-hydroxyproline side chain.

7. A pharmaceutical composition comprising:
   A. a polymeric compound comprising:
      1. a backbone which is a reaction product of;
         a. a poly(alkylene oxide); and
         b. a linking compound selected from the group consisting of lysine, argnine, etanolamine, and succinic acid; and
      2. one or more side chains directly conjugated to said linking compound of said backbone comprising:
         an antifibrotic agent selected from the group consisting of: cis-4-hydroxy-L-proline; 3,4-dehydro-L-proline; cis-4-fluoro-L-proline; cis-4-chloro-L-proline; laevo and cis isomers of compounds of the general structural formula:

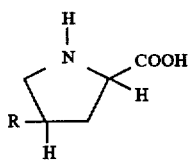

wherein R is OH, Cl, F, NH$_2$, SH, SCH$_3$, OCH$_3$, ONO$_2$, OSO$_2$, OSO$_3$H, H$_2$PO$_4$, or COOH; and pharmaceutically acceptable salts thereof; and
   B. a pharmaceutically acceptable carrier therefor.

8. A pharmaceutical composition in accordance with claim 7 in the form of a tablet, capsule, suspension, solution, liposome or aerosol.

9. A pharmaceutical composition in accordance with claim 7 in the form of an injectable suspension, solution or emulsion.

10. A pharmaceutical composition in accordance with claim 7 in the form of an injectable liposome composition.

* * * * *

UNITED STATES PATENT AND TRADEMARK OFFICE
CERTIFICATE OF CORRECTION

PATENT NO. : 5,720,950
DATED : February 24, 1998
INVENTOR(S) : George J. Poiani et al.

It is certified that error appears in the above-indentified patent and that said Letters Patent is hereby corrected as shown below:

In Claim 1 (column 35, line 10), "a poly(allcylene oxide)" should read

--a poly(alkylene oxide)--.

Signed and Sealed this

Fifth Day of May, 1998

*Attest:*

*Attesting Officer*

BRUCE LEHMAN

*Commissioner of Patents and Trademarks*

UNITED STATES PATENT AND TRADEMARK OFFICE
CERTIFICATE OF CORRECTION

PATENT NO. : 5,720,950
DATED : February 24, 1998
INVENTOR(S) : George J. Poiani; David J. Riley; Wei-Chi Liao; Joachim Kohn; and Keria Fiorella Gean It is certified that error appears in the above-indentified patent and that said Letters Patent is hereby corrected as shown below:

Title page, item [75],
Please correct the spelling of the fourth inventor "Joachim Kahn" to read --Joachim Kohn--.

Signed and Sealed this

Twenty-fifth Day of August, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,720,950
DATED : February 24, 1998
INVENTOR(S) : George J. Poiani; David J. Riley; Wei-Chi Liao; Joachim Kohn; and Keria Fiorella Gean It is certified that error appears in the above-identified patent and that said Letters Patent is hereby corrected as shown below:

<u>ON THE TITLE PAGE:</u>

Item [73] Assignee, please add --Rutgers University, Piscataway, NJ--.

Signed and Sealed this

Twenty-third Day of February, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO.    : 5,720,950
DATED         : February 24, 1998
INVENTOR(S)   : George J. Poiani et al.

It is certified that error appears in the above-identified patent and that said Letters Patent is hereby corrected as shown below:

<u>Column 3,</u>
Line 16, before "SUMMARY OF THE INVENTION," insert the following paragraph:

-- STATEMENT REGARDING FEDERALLY SPONSORED RESEARCH OR DEVELOPMENT
   This invention was made with government support under Grant No. HL2424 awarded by National Institutes of Health. The Government has certain rights in the invention. --

Signed and Sealed this

Eighth Day of July, 2003

JAMES E. ROGAN
*Director of the United States Patent and Trademark Office*